US011286294B2

(12) United States Patent
Lobo et al.

(10) Patent No.: US 11,286,294 B2
(45) Date of Patent: *Mar. 29, 2022

(54) ANTI-RSV MONOCLONAL ANTIBODY FORMULATION

(71) Applicant: MedImmune Ltd., Cambridge (GB)

(72) Inventors: Brian Lobo, Gaithersburg, MD (US); Deborah Goldberg, Gaithersburg, MD (US)

(73) Assignee: MEDIMMUNE LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/351,348

(22) Filed: Jun. 18, 2021

(65) Prior Publication Data

US 2021/0317191 A1    Oct. 14, 2021

Related U.S. Application Data

(60) Continuation of application No. 16/927,169, filed on Jul. 13, 2020, which is a division of application No. 15/907,876, filed on Feb. 28, 2018, now Pat. No. 10,774,133.

(60) Provisional application No. 62/465,379, filed on Mar. 1, 2017.

(51) Int. Cl.
*C07K 16/10* (2006.01)
*A61K 39/395* (2006.01)

(52) U.S. Cl.
CPC ........ *C07K 16/10* (2013.01); *A61K 39/39591* (2013.01); *C07K 16/1027* (2013.01); *C07K 2317/21* (2013.01); *C07K 2317/522* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,892,019 A | 4/1999 | Schlom et al. | |
| 8,562,996 B2 | 10/2013 | Spits et al. | |
| 8,568,726 B2 | 10/2013 | Beaumont et al. | |
| 9,283,274 B2 | 3/2016 | Beaumont et al. | |
| 9,321,831 B2 | 4/2016 | Spits et al. | |
| 10,016,496 B2 | 7/2018 | Ulbrandt | |
| 10,035,843 B2 | 7/2018 | Beaumont et al. | |
| 10,059,757 B2 | 8/2018 | Spits et al. | |
| 10,689,437 B2 | 6/2020 | Ulbrandt et al. | |
| 10,774,133 B2 * | 9/2020 | Lobo ...................... | A61P 11/00 |
| 2004/0170623 A1 | 9/2004 | Arvinte et al. | |
| 2007/0258981 A1 | 11/2007 | Hilbert et al. | |
| 2012/0121580 A1 | 5/2012 | Bhambhani et al. | |
| 2014/0348858 A1 | 11/2014 | Parra et al. | |
| 2016/0340414 A1 | 11/2016 | Ulbrandt et al. | |

| | | |
|---|---|---|
| 2018/0327484 A1 | 11/2018 | Spits et al. |
| 2019/0040120 A1 | 2/2019 | Beaumont et al. |
| 2019/0106482 A1 | 4/2019 | Ulbrandt et al. |

FOREIGN PATENT DOCUMENTS

| | | |
|---|---|---|
| AU | 2013201261 A1 | 3/2013 |
| EP | 2238985 A1 | 10/2010 |
| JP | 2005-508981 A | 4/2005 |
| JP | 2006-501168 A | 1/2006 |
| JP | 2015-522524 A | 8/2015 |
| WO | WO 1996/040252 A1 | 12/1996 |
| WO | WO 97/11177 A1 | 3/1997 |
| WO | WO 2003/039485 A2 | 5/2003 |
| WO | WO 2003/105894 A1 | 12/2003 |
| WO | WO 2003/106644 A2 | 12/2003 |
| WO | WO 2003/039485 A3 | 2/2004 |
| WO | WO 2004/091658 A1 | 10/2004 |
| WO | WO 2006/050280 A2 | 5/2006 |
| WO | WO 2008/147196 A2 | 12/2008 |
| WO | WO 2010/053883 A1 | 5/2010 |
| WO | WO 2011/017070 A1 | 2/2011 |
| WO | WO 2011/043643 A1 | 4/2011 |
| WO | WO 2013/076702 A2 | 5/2013 |
| WO | WO 2013/148686 A2 | 10/2013 |
| WO | WO 2013/164789 A2 | 11/2013 |
| WO | WO 2013/164789 A3 | 2/2014 |
| WO | WO 2014/036076 A1 | 3/2014 |
| WO | WO 2014/121021 A1 | 8/2014 |
| WO | WO 2015/108967 A2 | 7/2015 |
| WO | WO 2016/059512 A1 | 4/2016 |
| WO | WO 2017/005844 A1 | 1/2017 |
| WO | WO 2017/075124 A1 | 5/2017 |

(Continued)

OTHER PUBLICATIONS

Summary of Office Action and Search Report for Japanese Patent Application No. 2019-547310, dated Mar. 9, 2021, 1 page.
Chavez et al., "Improved Stability of a Model IgG3 by DoE-Based Evaluation of Buffer Formulations," *BioMed Research International*, vol. 2016, Article ID 2074149, 8 pages.
Clinical Trials.gov, "A study to Evaluate the Safety and Efficacy of MEDI8897 for the prevention of medically attended RSV LRTI in healthy preterm infants," Aug. 2016. Retrieved from the Internet: <URL:https://clinicaltrials.gov/ct2/show/study/NCT02878330>, [retrieved on Jul. 22, 2020], 8 pages.

(Continued)

*Primary Examiner* — Stacy B Chen

(74) *Attorney, Agent, or Firm* — Finnegan, Henderson, Farabow, Garrett & Dunner, LLP

(57) ABSTRACT

The present invention provides a formulation comprising: (i) an anti-RSV monoclonal antibody; and (ii) an ionic excipient; wherein the monoclonal antibody is present at a concentration of about 50 mg/ml or greater and the ionic excipient is present at a concentration of between 50 and 150 mM and the formulation has a pH of about 5.5 to about 7.5.

30 Claims, 3 Drawing Sheets

Specification includes a Sequence Listing.

(56) References Cited

FOREIGN PATENT DOCUMENTS

| WO | WO 2018/158332 A1 | 9/2018 |
| WO | WO 2018/160722 A1 | 9/2018 |

OTHER PUBLICATIONS

Dall'Acqua et al., "Properties of Human IgGls Engineered for Enhanced Binding to the Neonatal Fc Receptor (FcRn)," *The Journal of Biological Chemistry*, 2006; 281(33):23514-23524.

Domachowske et al., "Safety, tolerability and pharmacokinetics of MEDI8897, an extended half-life single-dose respiratory syncytial virus prefusion F-targeting monoclonal antibody administered as a single dose to healthy preterm infants," *The Pediatric Infectious Disease Journal*, Sep. 2018; 37(9):886-892.

Dubovsky, "Passive vaccination as a global strategy for preventing RSV disease in infants," Mar. 2016. Retrieved from the Internet: <URL:http://www.who.int/immunization/research/forums_and_initiatives/2_FDubovsky_Case_study_anti_RSV_mAbs_gvirf16.pdf?ua=1>, [retrieved on Oct. 24, 2017], 23 pages.

Extended European Search Report for European Patent Application No. 18761614.9, dated Nov. 24, 2020, 13 pages.

Ghosh, "ID Week 2015. San Diego, California, USA—Oct. 7-11, 2015," *Drugs of the Future*, 2015, 40(11):765-766.

Griffin et al., "Safety, Tolerability, and Pharmacokinetics of MEDI8897, the Respiratory Syncytial Virus Prefusion F-Targeting Monoclonal Antibody with an Extended Half-Life, in Health Adults," *Antimicrobial Agents and Chemotherapy*, Mar. 2017; 61(3):1-9.

Inoue et al., "Specific Decrease in Solution Viscosity of Antibodies by Arginine for Therapeutic Formulations," *Molecular Pharmaceutics*, 2014; 11(6):1889-1896.

International Search Report and Written Opinion, PCT Application No. PCT/US2018/020264, dated Jul. 5, 2018, 9 pages.

McLellan et al., "Structure of RSV Fusion Glycoprotein Trimer Bound to a Prefusion-Specific Neutralizing Antibody," *Science*, 2013; 340:1113-1117.

Robbie et al., "A Novel Investigational Fc-Modified Humanized Monoclonal Antibody, Motavizumab-YTE, has an Extended Half-Life in Healthy Adults," *Antimicrobial Agents and Chemotherapy*, 2013; 57(12):6147-6153.

Search and Examination Report for Great Britain Patent Application No. GB1802974.4, dated Oct. 30, 2018, 6 pages.

Zhu et al., "A Highly Potent Extended Half-Life Antibody as a Potential RSV Vaccine Surrogate for All Infants," *Science Translational Medicine*, 2017; 9(388):eaaj1928.

Information Disclosure Statement Transmittal Letter filed Dec. 20, 2018, for U.S. Appl. No. 16/003,455; 4 pages.

U.S. Office Action dated Mar. 18, 2019, for U.S. Appl. No. 16/003,455; 13 pages.

Applicant-Initiated Interview Summary dated Jun. 10, 2019, for U.S. Appl. No. 16/003,455; 6 pages.

Amendment and Response filed Aug. 1, 2019, for U.S. Appl. No. 16/003,455; 22 pages.

Ex parte Quayle Action issued Oct. 21, 2019, for U.S. Appl. No. 16/003,455; 7 pages.

Petition filed Dec. 29, 2019, for U.S. Appl. No. 16/003,455; 6 pages.

Petition Decision issued Mar. 5, 2020, for U.S. Appl. No. 16/003,455; 4 pages.

Amendment and Response filed Mar. 19, 2020, for U.S. Appl. No. 16/003,455; 8 pages.

Notice of Allowance dated Mar. 27, 2020, for U.S. Appl. No. 16/003,455; 5 pages.

Corrected Notice of Allowability dated May 21, 2020, for U.S. Appl. No. 16/003,455; 3 pages.

Wang et al. "Viscosity-lowering effect of amino acids and salts on highly concentrated solutions of two IgG1 monoclonal antibodies," Molecular Pharmaceutics, 2015, 12(12):4478-4487.

Kheddo et al., "The effect of arginine glutamate on the stability of monoclonal antibodies in solution," *Int J Pharmaceutics*, 2014, 473:126-133.

Lehermayr et al., "Assessment of net charge and protein-protein interactions of different monoclonal antibodies," *J Pharmaceutical Sciences*, 2011, 100(7):2551-2562.

Product Monograph, $^{Pr}$Synagis® palivizumab solution for injection, date of preparation: May 15, 2002; date of revision: Apr. 9, 2018, 42 pages.

Razinkov et al., "Accelerated formulation development of monoclonal antibodies (mAbs) and mAb-based modalities: review of methods and tools," *J Biomolecular Screening*, 2015, 20(4):468-483.

Wang, "Instability, stabilization, and formulation of liquid protein pharmaceuticals," *Int J Pharmaceutics*, 1999, 185:129-188.

\* cited by examiner

MEDI8897 heavy chain nucleotide sequences and translation

```
      Q   V   Q   L   V   Q   S   G   A   E   V   K   K   P   G   S   S   V   M   V
  1   CAA GTG CAG CTG GTG CAG TCT GGC GCC GAA GTG AAG AAA CCC GGC TCC TCC GTG ATG GTG

S   C   Q   A   S   G   G   L   L   E   D   Y   I   I   N   W   V   R   Q   A
 61   TCC TGC CAG GCT TCT GGC GGC CTG CTG GAA GAT TAC ATC ATC AAC TGG GTG CGA CAG GCC

P   G   Q   G   P   E   W   M   G   G   I   I   P   V   L   G   T   V   H   Y
121   CCA GGC CAG GGA CCT GAA TGG ATG GGC GGA ATC ATC CCC GTG CTG GGC ACC GTG CAC TAC

G   P   K   F   Q   G   R   V   T   I   T   A   D   E   S   T   D   T   A   Y
181   GGC CCT AAG TTC CAG GGC AGA GTG ACC ATC ACC GCC GAC GAG TCT ACC GAC ACC GCC TAC

M   E   L   S   S   L   R   S   E   D   T   A   M   Y   Y   C   A   T   E   T
241   ATG GAA CTG TCC TCC CTG CGG AGC GAG GAC ACC GCC ATG TAC TAC TGC GCC ACC GAG ACA

A   L   V   V   S   E   T   Y   L   P   H   Y   F   D   N   W   G   Q   G   T
301   GCC CTG GTG GTG TCC GAG ACA TAC CTG CCC CAC TAC TTC GAC AAC TGG GGC CAG GGA ACC

L   V   T   V   S   S | A   S   T   K   G   P   S   V   F   P   L   A   P   S
361   CTC GTG ACC GTC TCC TCA GCC TCC ACC AAG GGC CCA TCG GTC TTC CCC CTG GCA CCC TCC

S   K   S   T   S   G   G   T   A   A   L   G   C   L   V   K   D   Y   F   P
421   TCC AAG TCC ACC TCC GGC GGC ACC GCC GCT CTG GGC TGC CTG GTG AAG GAC TAC TTC CCT

E   P   V   T   V   S   W   N   S   G   A   L   T   S   G   V   H   T   F   P
481   GAG CCT GTG ACC GTG TCC TGG AAC TCT GGC GCC CTG ACC TCT GGC GTG CAC ACC TTC CCT

A   V   L   Q   S   S   G   L   Y   S   L   S   S   V   V   T   V   P   S   S
541   GCC GTG CTG CAG TCC TCC GGC CTG TAC TCC CTG TCC TCC GTG GTG ACA GTG CCT TCC TCC

S   L   G   T   Q   T   Y   I   C   N   V   N   H   K   P   S   N   T   K   V
601   TCC CTG GGC ACC CAG ACC TAC ATC TGC AAC GTG AAC CAC AAG CCC AGC AAC ACC AAG GTG

D   K   R   V   E   P   K   S   C   D   K   T   H   T   C   P   P   C   P   A
661   GAC AAG AGA GTT GAG CCC AAA TCT TGT GAC AAA ACT CAC ACA TGC CCA CCG TGC CCA GCA

P   E   L   L   G   G   P   S   V   F   L   F   P   P   K   P   K   D   T   L
721   CCT GAA CTC CTG GGG GGA CCG TCA GTC TTT CTG TTC CCT CCT AAG CCT AAG GAC ACC CTG (Y)  I  (T)  R  (E)  P   E   V   T   C   V   V   V   D   V   S   H   E   D   P
781   TAC  ATC ACC  CGG GAG  CCT GAA GTG ACC TGC GTG GTG GTG GAT GTG TCC CAC GAG GAC CCT

E   V   K   F   N   W   Y   V   D   G   V   E   V   H   N   A   K   T   K   P
841   GAG GTG AAG TTC AAT TGG TAC GTG GAC GGC GTG GAG GTG CAC AAC GCC AAG ACC AAG CCT

R   E   E   Q   Y   N   S   T   Y   R   V   V   S   V   L   T   V   L   H   Q
901   CGG GAG GAG CAG TAC AAC TCC ACC TAC CGG GTG GTG TCT GTG CTG ACC GTG CTG CAC CAG

D   W   L   N   G   K   E   Y   K   C   K   V   S   N   K   A   L   P   A   P
961   GAC TGG CTG AAC GGC AAA GAA TAC AAG TGC AAA GTC TCC AAC AAG GCC CTG CCT GCC CCC

I   E   K   T   I   S   K   A   K   G   Q   P   R   E   P   Q   V   Y   T   L
1021  ATC GAG AAA ACC ATC TCC AAA GCC AAA GGG CAG CCC CGA GAA CCA CAG GTG TAC ACC CTG

P   P   S   R   E   E   M   T   K   N   Q   V   S   L   T   C   L   V   K   G
1081  CCT CCC TCC CGC GAG GAG ATG ACC AAG AAC CAG GTG TCC CTG ACC TGT CTG GTG AAG GGC

F   Y   P   S   D   I   A   V   E   W   E   S   N   G   Q   P   E   N   N   Y
1141  TTC TAC CCT TCC GAT ATC GCC GTG GAG TGG GAG TCC AAC GGC CAG CCT GAG AAC AAC TAC

K   T   T   P   P   V   L   D   S   D   G   S   F   F   L   Y   S   K   L   T
1201  AAG ACC ACC CCT CCT GTG CTG GAC TCC GAC GGC TCC TTC TTC CTG TAC TCC AAG CTG ACC

V   D   K   S   R   W   Q   Q   G   N   V   F   S   C   S   V   M   H   E   A
1261  GTG GAC AAG TCC CGG TGG CAG CAG GGC AAC GTG TTC TCC TGC TCC GTG ATG CAC GAG GCT

L   H   N   H   Y   T   Q   K   S   L   S   L   S   P   G   K
1321  CTG CAC AAC CAC TAC ACC CAG AAA AGC CTC TCC CTG TCT CCG GGT AAA
```

(CDRs are underlined, amino acid differences from allelic constant regions have been circled and division between the variable and constant regions marked by a '|')

FIG. 1

MEDI8897 light chain nucleotide sequences and translation

```
      D   I   Q   M   T   Q   S   P   S   S   L   S   A   A   V   G   D   R   V   T
  1   GAC ATC CAG ATG ACC CAG TCC CCC TCC TCT CTG TCT GCT GCC GTG GGC GAC AGA GTG ACC

I   T   C   Q   A   S   Q   D   I   V   N   Y   L   N   W   Y   Q   Q   K   P
 61   ATC ACC TGT CAG GCC TCC CAG GAC ATC GTG AAC TAC CTG AAC TGG TAT CAG CAG AAG CCC

G   K   A   P   K   L   L   I   Y   V   A   S   N   L   E   T   G   V   P   S
121   GGC AAG GCC CCC AAG CTG CTG ATC TAC GTG GCC TCC AAC CTG GAA ACC GGC GTG CCC TCC

R   F   S   G   S   G   S   G   T   D   F   S   L   T   I   S   S   L   Q   P
181   AGA TTC TCC GGC TCT GGC TCT GGC ACC GAC TTC AGC CTG ACC ATC TCC AGC CTG CAG CCT

E   D   V   A   T   Y   Y   C   Q   Q   Y   D   N   L   P   L   T   F   G   G
241   GAG GAC GTG GCC ACC TAC TAC TGC CAG CAG TAC GAC AAC CTG CCC CTG ACC TTT GGC GGA

G   T   K   V   E   I   K   R   T   V   A   A   P   S   V   F   I   F   P   P
301   GGC ACC AAG GTG GAG ATC AAA CGA ACT GTG GCT GCA CCA TCT GTC TTC ATC TTC CCC CCC

S   D   E   Q   L   K   S   G   T   A   S   V   V   C   L   L   N   N   F   Y
361   AGC GAC GAG CAG CTG AAG AGC GGC ACC GCC TCC GTG GTG TGC CTG CTG AAC AAC TTC TAC

P   R   E   A   K   V   Q   W   K   V   D   N   A   L   Q   S   G   N   S   Q
421   CCC CGC GAG GCC AAG GTG CAG TGG AAG GTG GAC AAC GCC CTG CAG TCC GGC AAC AGC CAG

E   S   V   T   E   Q   D   S   K   D   S   T   Y   S   L   S   S   T   L   T
481   GAG AGC GTC ACC GAG CAG GAC AGC AAG GAC TCC ACC TAC AGC CTG AGC AGC ACC CTG ACC

L   S   K   A   D   Y   E   K   H   K   V   Y   A   C   E   V   T   H   Q   G
541   CTG AGC AAG GCC GAC TAC GAG AAG CAC AAG GTG TAC GCC TGC GAG GTG ACC CAC CAG GGC

L   S   S   P   V   T   K   S   F   N   R   G   E   C
601   CTG TCC AGC CCC GTG ACC AAG AGC TTC AAC AGG GGC GAG TGC
```

FIG. 2

ANTI-RSV MONOCLONAL ANTIBODY FORMULATION

CROSS-REFERENCE TO RELATED APPLICATIONS

This application is a continuation application of U.S. patent application Ser. No. 16/927,169, filed Jul. 13, 2020, which is a divisional application of U.S. patent application Ser. No. 15/907,876, filed Feb. 28, 2018, now U.S. Pat. No. 10,774,133, which claims the benefit of U.S. Provisional Application Ser. No. 62/465,379, filed Mar. 1, 2017, the disclosures of which are incorporated by reference herein in their entireties.

SEQUENCE LISTING

This application contains a Sequence Listing electronically submitted via EFS-Web to the United States Patent and Trademark Office as an ASCII text file entitled "0490-000005US03_ST25.txt" having a size of 13 kilobytes and created on Apr. 19, 2021. The information contained in the Sequence Listing is incorporated by reference herein.

FIELD OF THE INVENTION

The invention is concerned with an anti-RSV antibody formulation, in particular, an anti-RSV monoclonal antibody formulation and uses thereof. The invention also is concerned with an isolated anti-RSV monoclonal antibody and uses thereof.

BACKGROUND OF THE INVENTION

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5%> and 3.2% of children with RSV infection require hospitalization. Approximately 90,000 hospital admissions and 4,500 deaths per year were reported in United States. Major risk factors for hospitalization due to RSV are premature birth, chronic lung disease, congenital heart disease, compromised immunity, and age younger than 6 weeks in otherwise healthy children. There is a need for additional treatment for RSV positive bronchiolitis beside supportive care in the form of adequate nutrition and oxygen therapy. Antiviral therapies such as Ribavirin have not been proven to be effective in RSV infection. One monoclonal antibody, Palivizumab (also called Synagis<®>), is registered for prophylaxis against RSV infection, Palivizumab is a genetically engineered (humanized) monoclonal antibody to the fusion protein of RSV. While Palivizumab has been a very effective prophylactic, alternative antibodies and therapies providing additional coverage against RSV would be advantageous.

As a result of the isoelectric point (pI) of a number of anti-RSV monoclonal antibodies being in the preferred pharmaceutical pH formulation range for proteins (pH 5.5 to pH 7.5), these molecules present unique formulation challenges.

Colloidal instability at a molecules pI is due to a lack of an electrostatic charge on the molecule, which allows closer protein-protein interactions (so-called "self-association") that lead to physical instabilities. For this reason, the pH of a protein formulation is typically selected to be at least 1 pH unit away from the protein pI. This aims to provide colloidal stability and thus prevent the physical instabilities, such as aggregation, precipitation, opalescence, phase separation and/or particle formation.

According to the '1 pH unit away' rule, antibodies having a low or neutral pI e.g. pI of pH 5.5 to pH 7.5 thus should be formulated into a formulation with a pH outside the range of 5.5 to 7.5. However, outside this range, additional instabilities can be observed.

At more acidic pH, an increased rate of fragmentation reduced conformational stability and increased aggregation can be observed. At more basic pH, the potential for increased oxidation, deamidation and fragmentation and incompatibility with glass containers are present. The above instabilities are particularly problematic in such anti-RSV antibody formulations where the antibody is present at a commercially desirable concentration e.g. 50 mg/ml and above.

Therefore, there exists a need to provide an improved formulation for an anti-RSV antibody having a low or neutral pI. In particular, there exists a need to provide a stable formulation for an anti-RSV antibody having a low or neutral pI and, particularly such a formulation having a commercially desirable antibody concentration.

BRIEF SUMMARY OF THE INVENTION

The present invention provides a new anti-RSV antibody formulation, in particular a new anti-RSV monoclonal antibody formulation. In particular, the present formulation provides a means for improving colloidal stability for antibodies having a low or neutral pI. The present invention thus provides an alternative to the '1 pH away' rule for providing colloidal stability. The present invention thus allows antibodies having a low or neutral pI to be formulated within 1 pH unit of the antibody pI. Thus, the present invention enables such antibodies to be formulated within a pH range of 5.5 to 7.5 and at a commercially useful concentration, whilst substantially avoiding the instabilities associated with more acidic or more basic pHs.

The present invention further provides a new anti-RSV antibody MEDI8897. An improved pharmaceutically suitable formulation of the new anti-RSV antibody MEDI8897 is facilitated by formulating the antibody according to the teaching of the present invention.

The invention is particularly concerned with anti-RSV antibodies having a low or neutral pI, in particular the MEDI8897 antibody. MEDI8897 is a human IgG1κ-YTE monoclonal antibody directed against RSV-F protein.

MEDI8897 has a full length heavy chain sequence of FIG. 1 (SEQ ID NO: 2) and a full length light chain sequence of FIG. 2 (SEQ ID NO: 1).

MEDI8897 has CDR sequences: light chain CDR-L1 of QASQDIVNYLN (SEQ ID NO: 3), light chain CDR-L2 of VASNLET (SEQ ID NO: 4), light chain CDR-L3 of QQYDNLPLT (SEQ ID NO: 5), heavy chain CDR-H1 of DYIIN (SEQ ID NO: 6), heavy chain CDR-H2 of GIIPVLGTVHYGPKFQG (SEQ ID NO: 7), and heavy chain CDR-H3 of ETALVVSETYLPHYFDN (SEQ ID NO: 8). The 6 CDRS are underlined in FIGS. 1 and 2.

MEDI8897 has a light chain variable sequence of amino acid residues 1 to 107 of FIG. 1 (SEQ ID NO: 9) and a heavy chain variable sequence of amino acid residues 1 to 126 of FIG. 2 (SEQ ID NO: 10).

MEDI8897 pI was measured by cIEF to be 6.4 to 6.7, with the main peak at 6.4. The pI thus overlaps with the desired pharmaceutical formulation buffer range and suggests potential issues with manufacturing, formulation and storage stability if formulated within this range.

The invention provides a formulation comprising:
i. an anti-RSV monoclonal antibody; and
ii. an ionic excipient;

wherein the monoclonal antibody is present at a concentration of about 50 mg/ml or greater (e.g., about 50 mg/ml to about 200 mg/ml) and the ionic excipient is present at a concentration of about 50 to 150 mM and the formulation has a pH of about 5.5 to about 7.5.

In one embodiment, the anti-RSV monoclonal antibody has a low or neutral pI, for example in the range about pH 5.5 to about pH 7.5. In one embodiment, the monoclonal antibody has a pI in the range of about pH 6.0 to about pH 7.5. In one embodiment, the monoclonal antibody has a pI in the range of pH about 6.3 to about pH 7.5. In one embodiment, the monoclonal antibody has a pI in the range of about pH 6.4 to about pH 7.5. In one embodiment, the monoclonal antibody has a pI in the range of about pH 6.4 to about pH 6.7. In one embodiment, the monoclonal antibody has a pI of about pH 6.4. Without wishing to be bound by theory, a low to neutral pI can occur for proteins where there is a either a net balance of oppositely charged (positive amine groups and negative carboxylate groups) amino acid side chains on the protein or different domains have overall oppositely charge, within a pH range of about 5.5 to about 7.5. Again, without wishing to be bound by theory, it is possible that the ionic excipient in the formulation of the invention shields these opposing and attractive charges, thus colloidally stabilizing proteins having a pI within this range. The present invention thus provides use of an ionic excipient in an antibody formulation for the purpose of changing the charge state or distribution of the antibody in the formulation. The present invention further provides use of an ionic excipient in an antibody formulation for the purpose of colloidally stabilizing the antibody in the formulation.

In one embodiment, the monoclonal antibody is present in the formulations described herein at a concentration of about 75 mg/ml or greater (e.g., about 75 mg/ml to about 200 mg/ml). In one embodiment, the monoclonal antibody is present in the formulations described herein at a concentration of about 100 mg/ml or greater. In one embodiment, the anti-RSV monoclonal antibody is present in the formulations described herein at a concentration of about 100 mg/ml to about 165 mg/ml. In one embodiment, the anti-RSV monoclonal antibody is present at a concentration of about 100 mg/ml. In one embodiment, the ionic excipient is present at a concentration of about 75 mM to about 100 mM. In one embodiment, the ionic excipient is present at a concentration of about 75 mM. In one embodiment, the ionic excipient is present at a concentration of about 80 mM.

In one embodiment, the monoclonal antibody is an IgG1 monoclonal antibody. The invention thus provides a formulation comprising:
i. an IgG1 anti-RSV monoclonal antibody; and
ii. an ionic excipient;

wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5.

In one embodiment, the formulations described herein have a pH in the range of about pH 5.5 to about pH 6.5. In one embodiment, the formulations described herein have a pH in the range of about pH 5.7 to about pH 6.3. In one embodiment, the formulations described herein have a pH in the range of about pH 5.7 to about pH 6.1. Preferred formulations have a pH of about 5.8. Other preferred formulations have a pH of about 6.0.

In one embodiment, the ionic excipient is a charged amino acid. In one embodiment, the ionic excipient is lysine. In another embodiment, the ionic excipient is arginine.

In one embodiment, the ionic excipient is a salt. The invention thus provides a formulation comprising:
i. an anti-RSV monoclonal antibody as defined anywhere herein; and
ii. a salt;

wherein the monoclonal antibody is present at a concentration of about 50 mg/ml or greater and the salt is present at a concentration of about 50 to about 150 mM and the formulation has a pH of about 5.5 to about 7.5.

In one embodiment, the salt is present at a concentration of about 75 mM to about 100 mM. In one embodiment, the salt is present at a concentration of about 75 mM or about 80 mM.

In one embodiment, the salt is arginine hydrochloride, for example at a concentration of about 75 mM to about 100 mM, suitably at a concentration of about 80 mM.

In one embodiment, the formulation further comprises a sugar. Amongst other known benefits, the presence of a sugar can improve tonicity of the formulation. This is desirable since preferred formulations are isotonic or near isotonic. In one embodiment, the ionic excipient is a salt and the formulation further comprises a sugar.

The invention thus provides a formulation comprising:
i. an anti-RSV monoclonal antibody as defined anywhere herein;
ii. an ionic excipient (e.g. a salt) as defined anywhere herein;
iii. a sugar as defined anywhere herein; and wherein the monoclonal antibody is present at a concentration of about 50 mg/ml or greater and the ionic excipient is present at a concentration of about 50 to about 150 mM and the formulation has a pH of about 5.5 to about 7.5.

In one embodiment, the formulation further comprises a sugar and the ionic excipient is present at a concentration in the range of about 75 mM to less than 150 mM. In one embodiment, the formulation further comprises a sugar and the ionic excipient is present at a concentration in the range of about 75 mM to about 100 mM. In one embodiment, the formulation further comprises a sugar, which is present at a concentration in the range of about 100 mM to about 140 mM, and the ionic excipient is present at a concentration in the range of about 75 mM to about 100 mM.

In one embodiment, the sugar is sucrose, for example at a concentration of about 100 mM to about 140 mM, suitably at a concentration of about 120 mM.

In one embodiment, the formulation further comprises one or more buffers. In one embodiment, the one or more buffers is a buffer comprising histidine. In one embodiment, the one or more buffers are selected from a buffer comprising histidine succinate, histidine acetate, histidine citrate, histidine chloride or histidine sulfate. In one embodiment, the one or more buffers is histidine, histidine hydrochloride, or a combination thereof (histidine/histidine hydrochloride). In one embodiment, the one or more buffers is L-histidine/L-histidine hydrochloride monohydrate, for example at a concentration of about 10 mM to about 50 mM, suitably at a concentration of about 30 mM. It will be understood that a buffer may, itself, be an ionic excipient. Thus, in one embodiment, the buffer is the ionic excipient. In this embodiment, the concentration of the buffer should be above 50 mM i.e. in line with the concentration of the ionic excipient disclosed herein. Put another way, in one embodiment, the ionic excipient also acts as a buffer in the formulation. In this embodiment, an additional buffer may or may not be present.

In one embodiment, the formulation further comprises a surfactant. In one embodiment, the surfactant is a polysorbate, including for example, polysorbate-80.

In one embodiment, the formulation further comprises a sugar and one or more buffers. In one embodiment, the ionic excipient is a salt and the formulation further comprises a sugar and one or more buffers.

In one embodiment, the formulation further comprises a surfactant, a sugar and one or more buffers. In one embodiment, the ionic excipient is a salt and the formulation further comprises a surfactant, a sugar and one or more buffers.

The invention thus provides a formulation comprising:
i. an anti-RSV monoclonal antibody as defined anywhere herein;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein
wherein the monoclonal antibody is present at a concentration of about 50 mg/ml or greater and the ionic excipient is present at a concentration of about 50 to about 150 mM and the formulation has a pH of about 5.5 to about 7.5.

The invention also provides a formulation comprising:
i. an anti-RSV monoclonal antibody having a heavy chain variable region CDR1 sequence comprising a sequence which is at least 70% identical to the heavy chain variable region CDR1 sequence of MEDI 8897, and a heavy chain variable region CDR2 sequence comprising a sequence which is at least 70% identical to the heavy chain variable region CDR2 sequence of MEDI 8897, and a heavy chain variable region CDR3 sequence comprising a sequence which is at least 70% identical to the heavy chain variable region CDR3 sequence of MEDI 8897, and a light chain variable region CDR1 sequence comprising a sequence which is at least 70% identical to the light chain variable region CDR1 sequence of MEDI 8897, and a light chain variable region CDR2 sequence comprising a sequence which is at least 70% identical to the light chain variable region CDR2 sequence of MEDI 8897, and a light chain variable region CDR3 sequence comprising a sequence which is at least 70% identical to the light chain variable region CDR3 sequence of MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein
wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5. In one embodiment, the anti-RSV monoclonal antibody has a heavy chain variable region CDR1 sequence comprising a sequence which is at least 80% identical to the heavy chain variable region CDR1 sequence of MEDI 8897, and a heavy chain variable region CDR2 sequence comprising a sequence which is at least 80% identical to the heavy chain variable region CDR2 sequence of MEDI 8897, and a heavy chain variable region CDR3 sequence comprising a sequence which is at least 80% identical to the heavy chain variable region CDR3 sequence of MEDI 8897, and a light chain variable region CDR1 sequence comprising a sequence which is at least 80% identical to the light chain variable region CDR1 sequence of MEDI 8897, and a light chain variable region CDR2 sequence comprising a sequence which is at least 80% identical to the light chain variable region CDR2 sequence of MEDI 8897, and a light chain variable region CDR3 sequence comprising a sequence which is at least 80% identical to the light chain variable region CDR3 sequence of MEDI 8897. In one embodiment, the anti-RSV monoclonal antibody has a heavy chain variable region CDR1 sequence comprising a sequence which is at least 90% identical to the heavy chain variable region CDR1 sequence of MEDI 8897, and a heavy chain variable region CDR2 sequence comprising a sequence which is at least 90% identical to the heavy chain variable region CDR2 sequence of MEDI 8897, and a heavy chain variable region CDR3 sequence comprising a sequence which is at least 90% identical to the heavy chain variable region CDR3 sequence of MEDI 8897, and a light chain variable region CDR1 sequence comprising a sequence which is at least 90% identical to the light chain variable region CDR1 sequence of MEDI 8897, and a light chain variable region CDR2 sequence comprising a sequence which is at least 90% identical to the light chain variable region CDR2 sequence of MEDI 8897, and a light chain variable region CDR3 sequence comprising a sequence which is at least 90% identical to the light chain variable region CDR3 sequence of MEDI 8897. In one embodiment, the anti-RSV monoclonal antibody has a heavy chain variable region CDR1 sequence comprising a sequence which is at least 95% identical to the heavy chain variable region CDR1 sequence of MEDI 8897, and a heavy chain variable region CDR2 sequence comprising a sequence which is at least 95% identical to the heavy chain variable region CDR2 sequence of MEDI 8897, and a heavy chain variable region CDR3 sequence comprising a sequence which is at least 95% identical to the heavy chain variable region CDR3 sequence of MEDI 8897, and a light chain variable region CDR1 sequence comprising a sequence which is at least 95% identical to the light chain variable region CDR1 sequence of MEDI 8897, and a light chain variable region CDR2 sequence comprising a sequence which is at least 95% identical to the light chain variable region CDR2 sequence of MEDI 8897, and a light chain variable region CDR3 sequence comprising a sequence which is at least 95% identical to the light chain variable region CDR3 sequence of MEDI 8897.

The invention also provides a formulation comprising:
i. an anti-RSV monoclonal antibody having a heavy chain variable region CDR1 sequence which differs by no more than 1 amino acid from the heavy chain variable region CDR1 sequence of MEDI 8897, and a heavy chain variable region CDR2 sequence which differs by no more than 1 amino acid from the heavy chain variable region CDR2 sequence of MEDI 8897, and a heavy chain variable region CDR3 sequence which differs by no more than 1 amino acid from the heavy chain variable region CDR3 sequence of MEDI 8897, and a light chain variable region CDR1 sequence which differs by no more than 1 amino acid from the light chain variable region CDR1 sequence of MEDI 8897, and a light chain variable region CDR2 which differs by no more than 1 amino acid from the light chain variable region CDR2 sequence of MEDI 8897, and a light chain variable region CDR3 sequence comprising a sequence which which differs by no more than 1 amino acid from the light chain variable region CDR3 sequence of MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5.

The invention also provides a formulation comprising:
i. an anti-RSV monoclonal antibody having the 6 CDRs of MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein wherein the monoclonal antibody is present at a concentration of about 50 mg/ml or greater (e.g., about 50 mg/ml to about 200 mg/ml) and the ionic excipient is present at a concentration of about 50 to about 150 mM and the formulation has a pH of about 5.5 to about 7.5.

The invention thus provides a formulation comprising:
i. an anti-RSV monoclonal antibody having the VH and VL sequences of MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein wherein the monoclonal antibody is present at a concentration of about 50 mg/ml or greater and the ionic excipient is present at a concentration of about 50 to about 150 mM and the formulation has a pH of about 5.5 to about 7.5.

The invention thus provides a formulation comprising:
i. an anti-RSV monoclonal antibody having the full length heavy and light chain sequences of MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein wherein the monoclonal antibody is present at a concentration of about 50 mg/ml or greater (e.g., about 50 mg/ml to about 200 mg/ml) and the ionic excipient is present at a concentration of about 50 to about 150 mM and the formulation has a pH of about 5.5 to about 7.5.

The invention thus provides a formulation comprising:
i. anti-RSV monoclonal antibody MEDI 8897;
ii. an ionic excipient (e.g. a salt) as defined anywhere herein;
iii. a sugar as defined anywhere herein;
iv. one or more buffers as defined anywhere herein; and
v. optionally a surfactant as defined anywhere herein wherein the monoclonal antibody is present at a concentration of about 50 mg/ml or greater (e.g., about 50 mg/ml to about 200 mg/ml) and the ionic excipient is present at a concentration of about 50 to about 150 mM and the formulation has a pH of about 5.5 to about 7.5.

The invention provides a formulation comprising:
i. an anti-RSV monoclonal antibody;
ii. arginine hydrochloride;
iii. sucrose;
iv. L-histidine/L-histidine hydrochloride monohydrate; and
v. polysorbate-80 wherein the monoclonal antibody is present at a concentration of about 50 mg/ml or greater (e.g., about 50 mg/ml to about 200 mg/ml) and the arginine hydrochloride is present at a concentration of about 50 to about 150 mM and the formulation has a pH of about 5.5 to about 7.5. In one embodiment, the RSV monoclonal antibody has the 6 CDRs of MEDI 8897. In one embodiment, the RSV monoclonal antibody has the VH and VL sequences of MEDI 8897. In one embodiment, the RSV monoclonal antibody has the full length heavy and light chain sequences of MEDI 8897. In one embodiment, the RSV monoclonal antibody is MEDI 8897.

The invention provides a formulation comprising:
i. an anti-RSV monoclonal antibody;
ii. arginine hydrochloride;
iii. sucrose;
iv. L-histidine/L-histidine hydrochloride monohydrate; and
v. polysorbate-80 wherein the monoclonal antibody is present at a concentration of about 100 mg/mL and the arginine hydrochloride is present at a concentration of about 80 mM and the formulation has a pH of about 6.0. The sucrose preferably has a concentration of about 120 mM. The L-histidine/L-histidine hydrochloride monohydrate preferably has a concentration of about 30 mM. The polysorbate preferably has a concentration of between 0.02% and 0.04%, more preferably the concentration is 0.02%. In one embodiment, the RSV monoclonal antibody has the 6 CDRs of MEDI 8897. In one embodiment, the RSV monoclonal antibody has the VH and VL sequences of MEDI 8897. In one embodiment, the RSV monoclonal antibody has the full length heavy and light chain sequences of MEDI 8897. In one embodiment, the RSV monoclonal antibody is MEDI 8897.

The formulations described herein can also include one or more additional excipients, including for example, one or more sugars, salts, amino acids, polyols, chelating agents, emulsifiers and/or preservatives.

The formulations of the invention preferably are pharmaceutical formulations.

The present invention provides an isolated monoclonal antibody having light chain CDR sequences: CDR-L1 of SEQ ID NO: 3, CDR-L2 of SEQ ID NO: 4, CDR-L3 of SEQ ID NO: 5 and heavy chain CDR sequences: CDR-H1 of SEQ ID NO: 6, CDR-H2 of SEQ ID NO: 7, CDR-H3 of SEQ ID NO: 8. The present invention provides an isolated monoclonal antibody having a light chain variable region sequence of SEQ ID NO: 9 and a heavy chain variable region sequence of SEQ ID NO: 10. The present invention provides an isolated monoclonal antibody having the three CDRs of light chain variable region of sequence of SEQ ID NO: 9 and the three CDRs of heavy chain variable region sequence of SEQ ID NO: 10. The present invention provides an isolated monoclonal antibody having a light chain sequence of SEQ ID NO: 1 and a heavy chain sequence of SEQ ID NO: 2. Preferably, the antibody is an IgG1 antibody. The present invention provides novel and inventive monoclonal antibodies per se based on novel and inventive monoclonal antibody MEDI-8897 as disclosed herein. The present invention provides a hybridoma capable of expressing an isolated monoclonal antibody according to the present invention. The present invention provides a nucleic acid encoding an isolated monoclonal antibody according to the present invention. The present invention provides an expression vector comprising a nucleic acid according to the present invention. The present invention provides a host cell comprising an expression vector according to the present invention. The present invention provides a process for recombinantly producing an isolated monoclonal antibody according to the present invention comprising culturing the host cell under conditions such that the antibody is expressed. The present invention provides an isolated monoclonal antibody as defined herein for use as a medicament. The present invention provides an isolated monoclonal antibody as defined herein for use in the treatment of a disease. The present invention provides a method of treating a disease in a subject comprising administering an isolated monoclonal antibody as defined herein to the subject. The present invention provides a pharmaceutical composition comprising an isolated monoclonal antibody as defined herein. The present invention provides a pharmaceutical composition as defined herein for use as a medicament. The present invention provides a pharmaceutical composition as defined herein for use in the treatment of a disease. The present invention provides a method of treating a disease in a subject comprising administering a pharmaceutical composition as defined herein to the subject.

The present invention provides a pharmaceutical formulation as described anywhere herein for use as a medicament. The present invention provides a pharmaceutical formulation as described anywhere herein for use in the treatment or prevention of a disease.

The present invention provides a method of treating or preventing a disease in a subject comprising administering a pharmaceutical formulation as described anywhere herein to the subject. Also provided herein are methods of treating or preventing a disease in a subject by administering a therapeutically effective amount of a pharmaceutical formulation as described anywhere herein to the subject.

In one embodiment, the subject is a human. In one embodiment, the subject is a human under 2 years of age. In one embodiment, the subject is a premature baby under 6 weeks of age.

In one embodiment, the disease is a lower respiratory tract disease.

In one embodiment, the disease is RSV infection.

BRIEF DESCRIPTIONS OF THE DRAWINGS

FIG. 1 shows the MEDI8897 heavy chain nucleotide sequence (SEQ ID NO: 12) and translation (SEQ ID NO: 2).

FIG. 2 shows the MEDI8897 light chain nucleotide sequence (SEQ ID NO: 11) and translation (SEQ ID NO: 1).

DETAILED DESCRIPTION OF THE INVENTION

Figure 3:
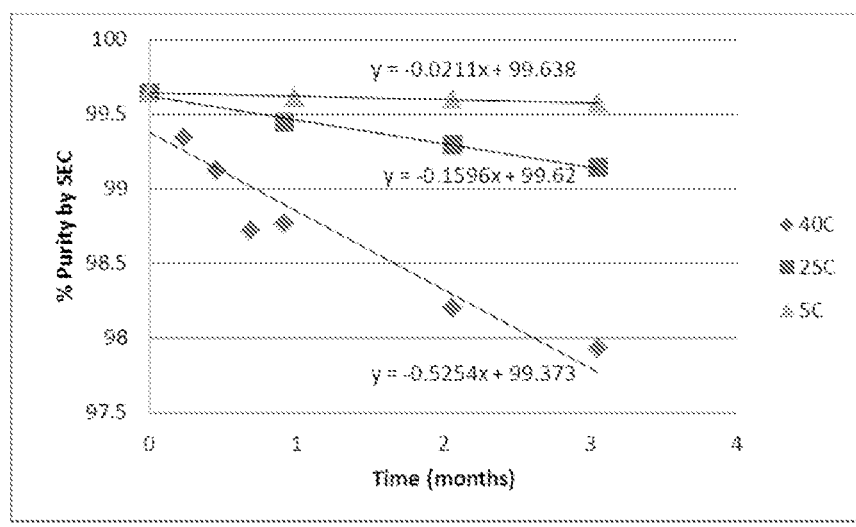
FIG. 3 shows MEDI8897 formulation stability over a 3 month period at 5° C., 25° C. and 40° C.

Due to the fact that a number of monoclonal antibodies possess a pI that is close to physiologic pH, i.e. the pH generally desired for human administration, difficulties in formulating these monoclonal antibodies occur. For such monoclonal antibodies, for the first time, the present invention provides motivation to formulate these 'difficult' antibodies as pharmaceuticals. Prior to the present invention, such antibodies might have been dismissed from being considered as drug candidates because of the lack of an appropriate formulation strategy for formulating at a commercially useful concentration and within a commercially useful pH range.

The present invention provides a new monoclonal antibody formulation. Suitably, the formulation has a pH that is within 1.0 pH unit below the isoelectric point of the monoclonal antibody.

The invention provides a formulation comprising: (i) an anti-RSV monoclonal antibody; and (ii) an ionic excipient (e.g. a salt); wherein the monoclonal antibody is present at a concentration of about 50 mg/ml or greater and the ionic excipient is present at a concentration of between 50 and 150 mM and the formulation has a pH of about 5.5 to about 7.5.

The invention further provides a formulation comprising: (i) an anti-RSV monoclonal antibody; and (ii) an ionic excipient (e.g. a salt); wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5; and wherein the aggregation rate of the monoclonal antibody in the formulation is reduced compared to the aggregation rate of the same antibody in the same formulation but without an ionic excipient.

Aggregation rate can be measured according to standard techniques as described herein. Surprisingly, formulations in accordance with the present invention have been shown to have good stability and to have decreased self-aggregation e.g. to exhibit≤2.0% aggregation when stored at room temperature for 3 months. The present invention thus provides the use of an ionic excipient in an antibody formulation for the purpose of increasing stability of the antibody in the formulation. The present invention further provides the use of an ionic excipient in an antibody formulation for the purpose of decreasing self-aggregation of the antibody in the formulation.

Antibody

The formulations of the present invention are particularly useful for anti-RSV antibodies having a low or neutral pI, for example in the range about pH 5.5 to about pH 7.5, about pH 6.0 to about pH 7.5, about pH 6.3 to about pH 7.5, or about pH 6.4 to about pH 7.5. The pI of an antibody can be measured according to standard techniques, for example by capillary isoelectric focusing (cIEF). The invention thus provides a formulation comprising: (i) a monoclonal antibody having a low or neutral pI; and (ii) an ionic excipient; wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5. The invention thus further provides a formulation comprising: (i) a monoclonal antibody having a low or neutral pI; and (ii) an ionic excipient; wherein the monoclonal antibody is present at a concentration of about 50 mg/ml or greater and the ionic excipient is present at a a concentration of about 50 to about 150 mM and the formulation has a pH of about 5.5 to about 7.5; and wherein the aggregation rate of the monoclonal antibody in the formulation is reduced compared to the aggregation rate of the same antibody in the same formulation but without an ionic excipient.

In one embodiment, the monoclonal antibody has a pI in the range of pH 6.4 to pH 7.5.

In one embodiment, the monoclonal antibody is an IgG1 or IgG4 monoclonal antibody. Most preferably, the monoclonal antibody is an IgG1 monoclonal antibody. The invention thus provides a formulation comprising: (i) an IgG1 monoclonal anti-RSV antibody having a low or neutral pI; and (ii) an ionic excipient; wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5. The invention thus further provides a formulation comprising: (i) an IgG1 monoclonal antibody having a low or neutral pI; and (ii) an ionic excipient; wherein the monoclonal antibody is present at a concentration of about 50 mg/ml or greater (e.g., about 50 mg/ml to about 200 mg/ml) and the ionic excipient is present at a a concentration of about 50 to about 150 mM and the formulation has a pH of about 5.5 to about 7.5; and wherein the aggregation rate of the monoclonal antibody in the formulation is reduced compared to the aggregation rate of the same antibody in the same formulation but without an ionic excipient.

The invention is particularly concerned with formulations comprising antibody MEDI-8897 or variants thereof. In one embodiment, the anti-RSV monoclonal antibody has a heavy chain variable region CDR1 sequence comprising a sequence which is at least 70% identical to the heavy chain variable region CDR1 sequence of MEDI 8897, and a heavy chain variable region CDR2 sequence comprising a sequence which is at least 70% identical to the heavy chain variable region CDR2 sequence of MEDI 8897, and a heavy chain variable region CDR3 sequence comprising a sequence which is at least 70% identical to the heavy chain variable region CDR3 sequence of MEDI 8897, and a light chain variable region CDR1 sequence comprising a sequence which is at least 70% identical to the light chain variable region CDR1 sequence of MEDI 8897, and a light chain variable region CDR2 sequence comprising a sequence which is at least 70% identical to the light chain variable region CDR2 sequence of MEDI 8897, and a light chain variable region CDR3 sequence comprising a sequence which is at least 70% identical to the light chain variable region CDR3 sequence of MEDI 8897.

In another embodiment, the anti-RSV monoclonal antibody has a heavy chain variable region CDR1 sequence comprising a sequence which is at least 80% identical to the heavy chain variable region CDR1 sequence of MEDI 8897, and a heavy chain variable region CDR2 sequence comprising a sequence which is at least 80% identical to the heavy chain variable region CDR2 sequence of MEDI 8897, and a heavy chain variable region CDR3 sequence comprising a sequence which is at least 80% identical to the heavy chain variable region CDR3 sequence of MEDI 8897, and a light chain variable region CDR1 sequence comprising a sequence which is at least 80% identical to the light chain variable region CDR1 sequence of MEDI 8897, and a light chain variable region CDR2 sequence comprising a sequence which is at least 80% identical to the light chain variable region CDR2 sequence of MEDI 8897, and a light chain variable region CDR3 sequence comprising a sequence which is at least 80% identical to the light chain variable region CDR3 sequence of MEDI 8897.

In one embodiment, the anti-RSV monoclonal antibody has a heavy chain variable region CDR1 sequence comprising a sequence which is at least 90% identical to the heavy chain variable region CDR1 sequence of MEDI 8897, and a heavy chain variable region CDR2 sequence comprising a sequence which is at least 90% identical to the heavy chain variable region CDR2 sequence of MEDI 8897, and a heavy chain variable region CDR3 sequence comprising a sequence which is at least 90% identical to the heavy chain variable region CDR3 sequence of MEDI 8897, and a light chain variable region CDR1 sequence comprising a sequence which is at least 90% identical to the light chain variable region CDR1 sequence of MEDI 8897, and a light chain variable region CDR2 sequence comprising a sequence which is at least 90% identical to the light chain variable region CDR2 sequence of MEDI 8897, and a light chain variable region CDR3 sequence comprising a sequence which is at least 90% identical to the light chain variable region CDR3 sequence of MEDI 8897.

In one embodiment, the anti-RSV monoclonal antibody has a heavy chain variable region CDR1 sequence comprising a sequence which is at least 95% identical to the heavy chain variable region CDR1 sequence of MEDI 8897, and a heavy chain variable region CDR2 sequence comprising a sequence which is at least 95% identical to the heavy chain variable region CDR2 sequence of MEDI 8897, and a heavy chain variable region CDR3 sequence comprising a sequence which is at least 95% identical to the heavy chain variable region CDR3 sequence of MEDI 8897, and a light chain variable region CDR1 sequence comprising a sequence which is at least 95% identical to the light chain variable region CDR1 sequence of MEDI 8897, and a light chain variable region CDR2 sequence comprising a sequence which is at least 95% identical to the light chain variable region CDR2 sequence of MEDI 8897, and a light chain variable region CDR3 sequence comprising a sequence which is at least 95% identical to the light chain variable region CDR3 sequence of MEDI 8897.

In another embodiment, the anti-RSV monoclonal antibody has a heavy chain variable region CDR1 sequence which differs by no more than 1 amino acid from the heavy chain variable region CDR1 sequence of MEDI 8897, and a heavy chain variable region CDR2 sequence which differs by no more than 1 amino acid from the heavy chain variable region CDR2 sequence of MEDI 8897, and a heavy chain variable region CDR3 sequence which differs by no more than 1 amino acid from the heavy chain variable region CDR3 sequence of MEDI 8897, and a light chain variable region CDR1 sequence which differs by no more than 1 amino acid from the light chain variable region CDR1 sequence of MEDI 8897, and a light chain variable region CDR2 which differs by no more than 1 amino acid from the light chain variable region CDR2 sequence of MEDI 8897, and a light chain variable region CDR3 sequence comprising a sequence which which differs by no more than 1 amino acid from the light chain variable region CDR3 sequence of MEDI 8897.

In another embodiment, the anti-RSV monoclonal antibody has the 6 CDRs of MEDI 8897.

In another embodiment, the anti-RSV monoclonal antibody has the 6 CDRs of MEDI 8897 in combination with 70% identity to the framework region sequences of MEDI 8897.

In another embodiment, the anti-RSV monoclonal antibody has the 6 CDRs of MEDI 8897 in combination with 80% identity to the framework region sequences of MEDI 8897.

In another embodiment, the anti-RSV monoclonal antibody has the 6 CDRs of MEDI 8897 in combination with 90% identity to the framework region sequences of

MEDI 8897.

In another embodiment, the anti-RSV monoclonal antibody has the 6 CDRs of MEDI 8897 in combination with 95% identity to the framework region sequences of MEDI 8897.

In one embodiment, the anti-RSV monoclonal antibody has the 6 CDRs of MEDI 8897 in combination with the changes to the heavy chain region of MEDI 8897 selected from those shown below in Table 1:

| Position Relative to SEQ ID NO. 2 | Amino Acid |
|---|---|
| 28 | P |
| 30 | R |
| 31 | N |
| 37 | L |
| 61 | A |
| 81 | I |
| 82 | H |
| 84 | I |
| 106 | T |

In one embodiment, the anti-RSV monoclonal antibody has the 6 CDRs of MEDI 8897 in combination with the changes to the heavy chain region of MEDI 8897 selected from those shown below in Table 2:

| Position Relative to SEQ ID NO. 2 | Amino Acid |
|---|---|
| 28 | P |
| 30 | R |
| 31 | N |
| 61 | A |
| 106 | T |

In one embodiment, the anti-RSV monoclonal antibody has the 6 CDRs of MEDI 8897 in combination with the changes to the heavy chain region of MEDI 8897 selected from those shown below in Table 3:

| Position Relative to SEQ ID NO. 2 | Amino Acid |
|---|---|
| 28 | P |
| 30 | R |
| 31 | N |
| 45 | L |
| 61 | A |
| 106 | T |

In one embodiment, the anti-RSV monoclonal antibody has the 6 CDRs of MEDI 8897 in combination with the changes to the heavy chain region of MEDI 8897 selected from those shown below in Table 4:

| Position Relative to SEQ ID NO. 2 | Amino Acid |
|---|---|
| 19 | K |
| 23 | K |
| 28 | T |
| 29 | F |
| 30 | S |
| 31 | N |
| 45 | L |
| 61 | A |
| 106 | T |

In one embodiment, the anti-RSV monoclonal antibody has the 6 CDRs of MEDI 8897 in combination with the changes to the heavy chain region of MEDI 8897 selected from those shown below in Table 5:

| Position Relative to SEQ ID NO. 2 | Amino Acid |
|---|---|
| 28 | P |
| 106 | T |

In one embodiment, the anti-RSV monoclonal antibody has the 6 CDRs of MEDI 8897 in combination with the changes to the heavy chain region of MEDI 8897 selected from those shown below in Table 6:

| Position Relative to SEQ ID NO. 2 | Amino Acid |
|---|---|
| 28 | P |
| 106 | T |
| 109 | R |

In one embodiment, the anti-RSV monoclonal antibody has the 6 CDRs of MEDI 8897 in combination with the changes to the heavy chain region of MEDI 8897 selected from those shown below in Table 7:

| Position Relative to SEQ ID NO. 2 | Amino Acid |
|---|---|
| 19 | K |
| 23 | K |
| 77 | S |
| 82 | H |
| 98 | R |
| 106 | T |

In one embodiment, the anti-RSV monoclonal antibody has the 6 CDRs of MEDI 8897 in combination with the changes to the heavy chain region of MEDI 8897 selected from those shown below in Table 8:

| Position Relative to SEQ ID NO. 2 | Amino Acid |
|---|---|
| 19 | K |
| 23 | K |
| 82 | H |
| 106 | T |

In one embodiment, the anti-RSV monoclonal antibody has the 6 CDRs of MEDI 8897 in combination with the changes to the heavy chain region of MEDI 8897 selected from those shown below in Table 9:

| Position Relative to SEQ ID NO. 2 | Amino Acid |
|---|---|
| 19 | K |
| 23 | K |
| 77 | S |
| 106 | T |

In one embodiment, the anti-RSV monoclonal antibody has the 6 CDRs of MEDI 8897 in combination with the changes to the heavy chain region of MEDI 8897 selected from those shown below in Table 10:

| Position Relative to SEQ ID NO. 2 | Amino Acid |
|---|---|
| 19 | K |
| 23 | K |
| 77 | S |

| Position Relative to SEQ ID NO. 2 | Amino Acid |
|---|---|
| 82 | H |
| 106 | T |

In another embodiment, the anti-RSV monoclonal antibody has the VH and VL sequences of MEDI 8897.

Preferably, the antibody is an IgG1 antibody.

Preferably, the anti-RSV monoclonal antibody defined anywhere herein has a heavy chain variable region CDR3 sequence ETALVVSETYLPHYFDN (SEQ ID NO: 8).

In one embodiment of the anti-RSV monoclonal antibody defined anywhere herein, the CDR3 of the heavy chain does not comprise the sequence ETALVVSTTYLPHYFDN. Preferably, any variant heavy chain variable region CDR3 sequences (i.e variants of SEQ ID NO: 8) in the anti-RSV monoclonal antibody defined anywhere herein retain E at the position marked by *: ETALVVS*TYLPHYFDN. Preferably, any variant heavy chain variable region CDR3 sequences (i.e variants of SEQ ID NO: 8) in the anti-RSV monoclonal antibody defined anywhere herein do not have T at the position marked by *: ETALVVS*TYLPHYFDN.

In an embodiment the anti-RSV monoclonal antibody has a modified Fc region wherein one or more amino acids has been inserted, deleted or substituted so as to increase the half-life of the antibody. In an embodiment, the anti-RSV monoclonal antibody has three amino acid substitutions (M252Y/S254T/T256E; called YTE) in the CH2 region of the Fc domain.

In another embodiment, the anti-RSV monoclonal antibody has the full length heavy and light chain sequences of MEDI 8897. Anti-RSV antibodies include antibody functional parts, e.g., antibodies or antigen-binding fragments, variants, or derivatives thereof. Anti-RSV antibodies further include, but are not limited to, polyclonal, monoclonal, human, humanized, or chimeric antibodies, single chain antibodies, bispecific antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody Concentration

Suitably, the monoclonal antibody is present in the formulations described herein at a concentration of about 50 mg/ml to about 300 mg/ml, about 50 mg/ml to about 200 mg/ml, about 100 mg/ml to about 200 mg/ml, about 100 mg/ml to about 165 mg/ml, about 100 mg/ml to about 150 mg/ml, or about 50 mg/ml, about 75 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, or about 200 mg/ml, including values and ranges within these ranges.

Suitably, the monoclonal antibody is present in the formulations described herein at a concentration of about 100 mg/ml to about 165 mg/ml. Suitably, the monoclonal antibody is present in the formulations described herein at a concentration of about 100 mg/ml.

pH

Suitably, the formulations described herein have a pH in the range of about pH 5.5 to about pH 6.5 in order to provide near optimal or optimal chemical stability (hydrolysis, deamidation, isomerization). In one embodiment, the formulations described herein have a pH in the range of about pH 5.7 to about pH 6.3. In one embodiment, the formulations described herein have a pH in the range of about pH 5.7 to about pH 6.1. Preferred formulations have a pH of about 5.8. Other preferred formulations have a pH of about 6.0.

Suitably, the formulations described herein have a pH in the range of about pH 5.5 to about pH 6.0, about pH 5.7 to about pH 6.0, or about pH 5.5, about pH 5.6, about pH 5.7, about pH 5.8, about pH 5.9, about pH 6.0, about pH 6.1, about pH 6.2, about pH 6.3, about pH 6.4, or about pH 6.5. In embodiments, the pH of the formulations provided herein is 5.7 to 6.0, more suitably the formulations have a pH of about 5.8.

A formulation pH close to about pH 7.4 also can be desirable for injection site tolerability.

Ionic Excipient

Exemplary ionic excipients for use in the formulations include salts and charged amino acids. The ionic excipient might comprise a combination of a salt and charged amino acid.

Exemplary charged amino acids include arginine and lysine.

Exemplary salts include salts of charged amino acids, for example, succinate, acetate, and sulfate salts of arginine and lysine.

Further, exemplary salts are those described herein including, but not limited to, sodium chloride, as well as other salts with sodium, potassium, calcium, magnesium and the like, such as chlorides, carbonates, sulphates, acetates, gluconates, lactates, malates, and other auxiliaries and the like which are customary in the field of parenteral administration. Suitably the salt is selected from sodium chloride (NaCl), lysine hydrochloride and arginine hydrochloride. In one embodiment, the salt is NaCl. In another embodiment, the salt is arginine hydrochloride.

The concentration of the ionic excipient, suitably salt, in the pharmaceutical formulations described herein is generally in the range of about 50 mM to about 300 mM, more suitably about 50 mM to about 200 mM, about 50 mM to about 150 mM, about 50 mM to about 100 mM, about 60 mM to about 80 mM, or about 50 mM, about 55 mM, about 60 mM, about 65 mM, about 70 mM, about 75 mM, about 80 mM, about 85 mM, about 90 mM, about 95 mM or about 100 mM, including any ranges or values within these ranges. In one embodiment, the ionic excipient is present at a concentration of about 50 mM to about 125 mM.

In one embodiment, the ionic excipient is present at a concentration of about 50 mM to about 100 mM.

In one embodiment, the ionic excipient is present at a concentration of about 75 mM to about 100 mM.

In suitable embodiments, the salt is NaCl, for example at a concentration of about 50 mM to about 100 mM, suitably at a concentration of about 70 mM.

In suitable embodiments, the salt is arginine hydrochloride, for example at a concentration of about 50 mM to about 100 mM, suitably at a concentration of about 80 mM.

Buffers

The formulations described herein suitably comprise one or more buffers. As used herein, "buffer" refers to an excipient for maintaining the pH of a formulation. Exemplary buffers for use in the formulations provided herein include, but are not limited to histidine, histidine hydrochloride (histidine HCl), sodium succinate, sodium acetate, sodium acetate/acetic acid, sodium phosphate, citrate, phosphate, succinate, glycine, and acetate. In one embodiment, the buffer for use in the formulations described herein is sodium acetate/acetic acid. In one embodiment, the one or more buffers is a buffer comprising histidine. In one embodiment, the one or more buffers are selected from a buffer comprising histidine succinate, histidine acetate, histidine citrate, histidine chloride or histidine sulfate. In one embodiment, the one or more buffers is histidine, histidine hydrochloride, or a combination thereof (histidine/histidine hydrochloride). In one embodiment, the one or more buffers is L-histidine/L-histidine hydrochloride monohydrate.

The concentration of a buffer, suitably sodium acetate/acetic acid, in the pharmaceutical formulations described herein is generally in the range of about 10 mM to about 100 mM, more suitably about 15 mM to about 80 mM, about 25 mM to about 75 mM, about 30 mM to about 60 mM, about 40 mM to about 60 mM, about 40 mM to about 50 mM, or about 15 mM, about 20 mM, about 25 mM, about 30 mM, about 35 mM, about 40 mM, about 45 mM, about 50 mM, about 55 mM, about 60 mM, about 65 mM, about 70 mM or about 75 mM, including any ranges or values within these ranges.

In one embodiment, the one or more buffers is L-histidine/L-histidine hydrochloride monohydrate, for example at a concentration of about 10 mM to about 50 mM, suitably at a concentration of about 30 mM.

The pH of the buffer is preferably in the range of pH5.5 to pH6.0.

It will be understood that a buffer may, itself, be an ionic excipient. Thus, in one embodiment, the buffer is the ionic excipient. In this embodiment, the concentration of the buffer should be above 50 mM i.e. in line with the concentration of the ionic excipient disclosed herein. Preferable concentrations for the buffer in this embodiment are as discussed anywhere herein in relation to the ionic excipient.

Put another way, in one embodiment, the ionic excipient also acts as a buffer in the formulation. In this embodiment, an additional buffer may or may not be present.

Sugars and Surfactants

The formulations described herein suitably comprise a sugar, for example, but not limited to, trehalose, lactose, mannitol, melibiose, melezitose, raffinose, mannotriose, stachyose and sucrose. In other embodiments, a polyol such as trihydric or higher molecular weight sugar alcohols, e.g. glycerin, dextran, erythritol, glycerol, arabitol, xylitol, sorbitol, and mannitol, can be used. Examples of reducing sugars include, but are not limited to, glucose, maltose, maltulose, iso-maltulose and lactulose. Examples of non-reducing sugars include, but are not limited to, trehalose, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In one embodiment, the sugar is selected from the group consisting of trehalose, lactose, mannitol, raffinose and sucrose. In specific embodiments, trehalose is used as a sugar in the formulations described herein. In specific embodiments, sucrose is used as a sugar in the formulations described herein.

Suitably, the amount of sugar, for example trehalose, in a formulation described herein is about 1% (w/v) to about 10% (w/v). Unless otherwise noted, percentage of a component (%) is used herein indicate a weight/volume (w/v) %. In exemplary embodiments, the amount of sugar in a pharmaceutical formulation described herein is about 1% (w/v) to about 8% (w/v), or about 2% (w/v) to about 6% (w/v), about 2% (w/v) to about 5% (w/v), about 3% (w/v) to about 5% (w/v), or about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v), including any values and ranges within these ranges.

The formulations described herein suitably comprise a surfactant.

The term "surfactant" as used herein refers to organic substances having amphipathic structures; namely, they are composed of groups of opposing solubility tendencies, typically an oil- soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical formulations and preparations of biological materials. Pharmaceutically acceptable surfactants like polysorbates (e.g. polysorbates 20, 40, 60 or 80); polyoxamers (e.g. poloxamer 188); Triton; sodium octyl glycoside; lauryl-, myristyl-, linoleyl- , or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g. Pluronics, PF68 etc), can be used in the pharmaceutical formulations described herein. Suitably the surfactant is a polysorbate, including for example, polysorbate-20, polysorbate-40, polysorbate-60, and polysorbate-80. In one embodiment, the surfactant is polysorbate-80.

Suitably, the formulations described herein comprise a surfactant (suitably polysorbate-80) at about 0.001% to about 0.5% (w/v), more suitably about 0.002% to about 0.1% of a surfactant, for example about 0.01% to about 0.2%, about 0.02% to about 0.1%, about 0.02% to about 0.07%, about 0.03% to about 0.06%, about 0.04% to about 0.06%, or about 0.02%, about 0.025%, about 0.03%, about 0.035%, about 0.04%, about 0.045%, about 0.05%, about 0.055%, about 0.060%, about 0.065%, about 0.07%, about 0.075%, about 0.08%, about 0.085%, about 0.09%, about 0.095%, or about 0.1% of a surfactant, including any ranges or values within these ranges.

The formulations described herein suitably comprise a surfactant and a sugar. The formulations described herein suitably comprise a surfactant and one or more buffers. The formulations described herein suitably comprise a sugar and one or more buffers. The formulations described herein suitably comprise a surfactant, a sugar, and one or more buffers.

The formulations described herein can also include one or more additional excipients, including for example, one or more sugars, salts, amino acids, polyols, chelating agents, emulsifiers and/or preservatives.

Pharmaceutical Use

The formulations of the invention preferably are pharmaceutical formulations. Suitably, the pharmaceutical formulations described herein are "pharmaceutically acceptable," and thus would meet the necessary approval requirements required by a regulatory agency of the Federal or a state government, or listed in the U.S. Pharmacopeia, European Pharmacopeia, or other generally recognized pharmacopeia, so as to be used in animals, and more particularly in humans.

The present invention provides a pharmaceutical formulation as described anywhere herein for use as a medicament. The present invention provides a pharmaceutical formulation as described anywhere herein for use in the treatment of a disease. The present invention provides a method of treating a disease in a subject comprising administering a pharmaceutical formulation as described anywhere herein to the subject. Also provided herein are methods of treating a subject by administering a therapeutically effective amount of a pharmaceutical formulation as described anywhere herein to the subject.

As used herein, the term "subject" includes any human or nonhuman animal. The term "nonhuman animal" includes all vertebrates, for example, but not limited to, mammals and non-mammals, such as nonhuman primates, sheep, dogs, cats, horses, cows, chickens, amphibians, reptiles, etc. In one embodiment, the subject is a human.

The present invention provides a method of treating or preventing a disease in a subject comprising administering a pharmaceutical formulation as described anywhere herein to the subject. Also provided herein are methods of treating or preventing a disease in a subject by administering a therapeutically effective amount of a pharmaceutical formulation as described anywhere herein to the subject.

In one embodiment, the subject is a human. In one embodiment, the subject is a human under 2 years of age. In one embodiment, the subject is a premature baby under 6 weeks of age.

In embodiments, the formulation is administered to a subject subcutaneously or by injection.

Suitably, the formulations are a liquid formulation or a frozen formulation.

Also provided herein are methods of preparing a pharmaceutical formulation comprising preparing a pharmaceutical formulation as described herein, and suitably loading the pharmaceutical formulation into a syringe to form a pre-filled syringe.

Suitably, the pharmaceutical formulations described herein are prepared in sterile water, or are resuspended in sterile water for injection at the desired volume.

In exemplary embodiments, the pharmaceutical formulations have a volume of about 0.1 mL to about 20.0 mL, more suitably about 0.5 mL to about 15.0 mL, about 0.5 mL to about 12.0 mL, about 1.0 mL to about 10.0 mL, about 1.0 mL to about 5.0 mL, about 1.0 mL to about 2.0 mL or about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 2.1 mL, about 2.2 mL, about 2.3 mL, about 2.4 mL, about 2.5 mL, about 2.6 mL, about 2.7 mL, about 2.8 mL, about 2.9 mL, or about 3.0 mL, including any ranges or values within these ranges.

While in suitable embodiments, the pharmaceutical formulations described herein are liquid formulations, i.e., pharmaceutical formulations prepared in sterile water or water for injection (WFI), the pharmaceutical formulations can also be frozen formulations or previously lyophilized formulations.

The present invention also provides a lyophilized cake which is capable of being reconstituted using only sterile water into a formulation according to the invention as described herein. It will be understood that the ratio of antibody: ionic excipient will be the same in the lyophilized cake as in the post-lyophilized formulation. In one embodiment, the ratio of antibody: ionic excipient is in the range 450:1 to 40:1. Where the formulation has been lyophilized, the concentrations provided herein for the formulation are the post-reconstitution concentrations and thus are the concentrations in the so-called 'drug product'. By way of example, if a half-reconstitution strategy is used (where half the volume of water removed during lyophilization is returned during reconstitution), then after reconstitution, the concentration of the antibody will be twice what it was prior to lyophilization i.e. twice what is was in the so-called pre-lyophilization 'drug-substance' composition. It will therefore be understood that the present invention further provides a composition capable of being lyophilized to form a lyophilized cake, wherein the lyophilized cake is capable of being reconstituted using only sterile water into a formulation according to the invention as described herein. Suitable reconstitution strategies will be known to those skilled in the art. In embodiments, it is desirable to prepare frozen formulations by providing a liquid pharmaceutical formulation as described herein, and freezing the formulation under appropriate conditions. For example, the frozen formulations can be provided by freezing the liquid formulations to less than 0° C., more suitably to about −20° C., about −40° C., about −60° C., or suitably to about −80° C. The pharmaceutical formulations are also suitably prepared as liquid formulations and stored about 2° C. to about 8° C., or about 2° C., about 3° C., about 4° C., about 5° C., about 6° C., about 7° C. or about 8° C.

Suitable protocols and methods for preparing lyophilized pharmaceutical formulations from liquid and/or frozen formulations are known in the art.

Stability of Formulations

In exemplary embodiments, the formulations described herein are stable for extended periods of storage at room temperature or at a temperature range of about 2° C. to about 8° C., suitably about 5° C. As used herein, room temperature is generally in the range of about 22° C. to about 25° C. Suitably the pharmaceutical formulations are stable after storage at about 2° C. to about 8° C. (e.g. 5° C.) for at least six (6) months. As used herein, the term "stable" for a period of storage (or "stability") is used to indicate that the formulations resist aggregation, degradation, half antibody formation, and/or fragmentation. The stability of the monoclonal antibodies can be assessed by degrees of aggregation, degradation, half antibody formation or fragmentation, as measured by high performance size exclusion chromatography (HPSEC), static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference.

The overall stability of a pharmaceutical formulation comprising monoclonal antibodies can be assessed by various immunological assays including, for example, ELISA and radioimmunoassay using isolated antigen molecules.

The phrase "low to undetectable levels of aggregation" as used herein refers to pharmaceutical formulations containing no more than about 5%, no more than about 4%, no more than about 3%, no more than about 2%, no more than about 1%, or no more than about 0.5% aggregation by weight of protein as measured by high performance size exclusion chromatography (HPSEC) or static light scattering (SLS) techniques. Suitably, the pharmaceutical formulations exhibit≤5.0% aggregation, more suitably≤4.0% aggregation, ≤3.0% aggregation, ≤2.0% aggregation, ≤1.0% aggregation, or 0.5% aggregation. Suitably, the liquid pharmaceutical formulations and/or frozen pharmaceutical formulations exhibit≤5.0% aggregation, more suitably≤4.0% aggregation, ≤3.0% aggregation, ≤2.0% aggregation, ≤1.0% aggregation, or 0.5% aggregation.

The term "low to undetectable levels of fragmentation" as used herein refers to pharmaceutical formulations containing equal to or more than about 80%, about 85%, about 90%, about 95%, about 98%, or about 99% of the total monoclonal antibody, for example, in a single peak as determined by HPSEC, or reduced Capillary Gel Electrophoresis (rCGE), representing the non-degraded monoclonal antibody, or a non-degraded fragment thereof, and containing no other single peaks having more than about 5%, more than about 4%, more than about 3%, more than about 2%, more than about 1%, or more than about 0.5% of the total monoclonal antibody. Fragmentation may be measured suitably in IgG4 monoclonal antibodies.

Without wishing to be bound by theory, it is thought that decreased self-aggregation is due to improved colloidal stability, as evidenced by increased kD value.

In exemplary embodiments, the formulations described herein have reduced opalescence and decreased phase separation as visual observation, light scattering, nephelometry and turbidimetric methods.

Further embodiments, features, and advantages of the embodiments, as well as the structure and operation of the various embodiments, are described in detail below with reference to accompanying drawings.

EXAMPLES

Example 1

IgG1 Formulation

MEDI8897 is a human IgG1κ-YTE monoclonal antibody directed against RSV-F protein. Three amino acid substitutions (M252Y/S254T/T256E; called YTE) in the CH2 region of the Fc domain were introduced to increase the serum half-life of MEDI8897. Sequence information for MEDI8897 is provided in FIGS. 1 and 2. MEDI8897 pI was measured by cIEF to be 6.4-6.7 with the main peak at 6.4. The pI overlaps with the formulation buffer range (5.5-6.5) suggesting potential issues with manufacturing, formulation and storage stability.

MEDI8897 thermal stability was measured by differential scanning calorimetry. Tm1 was found to be 61° C. while Tm2 was 82° C. Tm1 of 61° C. meets the CDTP criteria of Tm1>50° C.

Stability Summary

Upon receipt of MEDI8897 in the default developability buffer (25 mM Histidine, 7% sucrose, pH 6.0), phase separation was observed at 2 to 8° C. The supernatant layer had a protein concentration of 75 mg/ml while the bottom layer was 125 mg/ml. Upon equilibration at 25° C. the two distinct phases disappeared and only one single phase was observed. The phase separation at 2 to 8° C. was thought to be due to the pI of MEDI8897 which is close to the formulation pH of 6.0. A scouting study was initiated to find a more appropriate formulation buffer for MEDI8897 stability assessment, targeting a condition which maintained solubility and prevented phase separation of MEDI8897 at 100 mg/ml.

Formulating in the default developability buffer (25 mM histidine, 7% sucrose) at pH's <5.9 or >6.7 mitigated phase separation. Addition of 75 mM NaCl to the developability buffer between pH 5.0 and 6.7 also mitigated phase separation. Finally, acetate and phosphate buffers at pH values away from the pI also mitigated phase separation. Based on these screening studies and previous knowledge of mAb's with pI's within the formulation space, an alternate developability buffer (25 mM His/HisHCl, 75 mM NaCl, 4% Sucrose, 0.02% PS80, pH 6.0) was selected for evaluation.

kD Studies

For the first kD screen, all samples were evaluated in 25 mM Histidine pH 5.5 base buffer from 2-10 mg/ml at 25° C. This buffer was chosen in lieu of pH 6.0 because MEDI8897 is more soluble at pH 5.5, facilitating DLS measurements which are sensitive to insoluble particles. Ionic excipients including arginine-HCl, lysine-HCl and NaCl were evaluated at 10, 25, 50, 75 and 100 mM concentrations. In addition, proline, alanine, $Na_2SO_4$ and histidine were evaluated at the 100 mM concentration only. Finally, 2, 4, and 6% sucrose were evaluated to determine if sucrose influences protein-protein interactions. All conditions were compared to a buffer control (25 mM Histidine pH 5.5).

The control samples showed distinct protein-protein interactions, with the hydrodynamic radius increasing from 6.2 to 7.8 nm from 2-10 mg/ml. Arginine-HCl, lysine-HCl and NaCl showed reduction of protein-protein interactions starting at 25 mM concentrations as evidenced by no increase in hydrodynamic size over the 2-10 mg/ml concentration range. No additional effects were seen between 25 and 100 mM. At 100 mM concentration, proline and alanine showed PPI similar to the control while $Na_2SO_4$ and Histidine mitigated PPI. Finally, sucrose concentration showed no impact on PPI.

This data illustrates that charged excipients (Arg-HCl, Lys-HCl, Histidine and $Na_2SO_4$) mitigate protein-protein interactions while neutral excipients (sucrose, proline, alanine) do not mitigate PPI. Therefore, addition of ionic excipients at pH 5.5 reduced phase separation at 100 mg/ml. 40° C. Stability Evaluation Based on kD screening, several conditions were selected for 40° C. stability evaluation. Table 11 summarizes the formulation conditions and 1 month degradation rates seen at 40° C.

TABLE 11

40° C. Stability Rates, Formulation Screen 1 - Excipient Screening

| Number | Excipient | Conc (mM) | % Mon/mo | % Agg/mo | % Frag/mo |
|---|---|---|---|---|---|
| 1 | NaCl | 25 | −5.9 | 4.2 | 1.8 |
| 2 | NaCl | 75 | −6.1 | 4.1 | 1.9 |
| 3 | NaCl | 95 | −5.4 | 3.5 | 1.9 |
| 4 | NaCl | 120 | −5.4 | 3.5 | 1.9 |
| 5 | Arg-HCl | 25 | −5.4 | 3.5 | 1.8 |
| 6 | Arg-HCl | 75 | −4.8 | 2.8 | 2.0 |
| 7 | Arg-HCl | 95 | −4.5 | 2.6 | 1.9 |
| 8 | Arg-HC1 | 120 | −4.8 | 2.8 | 2.0 |
| 9 | Lys-HCl | 25 | −5.7 | 3.9 | 1.9 |
| 10 | Lys-HCl | 75 | −5.0 | 2.7 | 2.3 |
| 11 | Lys-HCl | 95 | −5.1 | 3.1 | 2.0 |
| 12 | Lys-HC1 | 120 | −4.9 | 2.9 | 2.0 |

Base buffer for this study was 25 mM Histidine pH 6.0

This study illustrates that arginine and lysine are more stabilizing than NaCl. In addition, 75 mM and above appears to stabilize against aggregation. Based on this study, arginine was selected as the most stabilizing lyo-friendly excipient and was moved forward to the next set of studies.

Drug Product Stability on Final Lyo Cycle/Representative Material

Stability was evaluated in formulation sciences to complement the IND-enabling stability studies as this was the first representative material to complete the lyophilization step. Three months of data was collected for the post reconstitution formulation of 100 mg/ml in 30 mM L-histidine/L-histidine hydrochloride monohydrate, 80 mM L-arginine hydrochloride, 120 mM sucrose, 0.04% (w/v) polysorbate 80, pH 6.0. Results are shown in FIG. 3. Storage at 2-8° C. showed virtually no change during the 3 month period, confirming the suitability of the formulation and lyo cycle for clinical use. These data thus demonstrate that the formulation provides appropriate stability and solubility and is suitable as a cycle 1 formulation.

TABLE 12

Drug Product Stability 3 Month Data Summary

| Temperature | HIAC (≥10 μm) | HIAC (≥25 μm) | Bioassay | Recon Time | VI | KF |
|---|---|---|---|---|---|---|
| 2-8° C. | 216 | 108 | 97% | 2 min | <STD1 | 1.3% |
| 25° C. | 522 | 90 | 97% | 3 min | <STD1 | 1.4% |
| 40° C. | 126 | 0 | 90% | 3 min | <STD2 | 1.7% |

All documents, patents, journal articles and other materials cited in the present application are hereby incorporated by reference.

Although the present invention has been fully described in conjunction with several embodiments thereof with reference to the accompanying drawings, it is to be understood that various changes and modifications can be apparent to those skilled in the art. Such changes and modifications are to be understood as included within the scope of the present invention as defined by the appended claims, unless they depart there from.

The invention may be further defined by reference to the following numbered paragraphs.

Paragraph 1. A formulation comprising:
   i. An anti-RSV monoclonal antibody; and
   ii. an ionic excipient;
   wherein the monoclonal antibody is present at a concentration of about 50 mg/ml or greater (e.g., about 50 mg/ml to about 200 mg/ml, to about 175 mg/ml, to about 165 mg/ml, to about 150 mg/1 or to about 125 mg/ml) and the ionic excipient is present at a a concentration of about 50 to about 150 mM and the formulation has a pH of about 5.5 to about 7.5.

Paragraph 2. A formulation according to paragraph 1, wherein the monoclonal antibody has a pI in the range of pH 6.4 to pH 7.5.

Paragraph 3. A formulation according to paragraph 1 or paragraph 2, wherein the monoclonal antibody has a pI in the range of about pH 6.4.

Paragraph 4. A formulation according to any one of the preceding paragraphs, wherein the monoclonal antibody is an IgG1 monoclonal antibody.

Paragraph 5. A formulation according to any one of the preceding paragraphs, wherein the monoclonal antibody has light chain CDR sequences:
CDR-L1 of SEQ ID NO: 3
CDR-L2 of SEQ ID NO: 4
CDR-L3 of SEQ ID NO: 5
and heavy chain CDR sequences:
CDR-H1 of SEQ ID NO: 6
CDR-H2 of SEQ ID NO: 7
CDR-H3 of SEQ ID NO: 8.

Paragraph 6. A formulation according to any one of the preceding paragraphs, wherein the monoclonal antibody has a light chain variable region sequence of SEQ ID NO: 9 and a heavy chain variable region sequence of SEQ ID NO: 10.

Paragraph 7. A formulation according to any one of the preceding paragraphs, wherein the monoclonal antibody has a light chain sequence of SEQ ID NO: 1 and a heavy chain sequence of SEQ ID NO: 2.

Paragraph 8. A formulation according to any one of the preceding paragraphs, wherein the monoclonal antibody is present in the formulation at a concentration of about 100 mg/ml to about 165 mg/ml.

Paragraph 9. A formulation according to paragraph 8, wherein the monoclonal antibody is present in the formulation at a concentration of about 100 mg/ml.

Paragraph 10. A formulation according to any one of the preceding paragraphs, wherein the formulation has a pH in the range of about pH 5.7 to about pH 6.1.

Paragraph 11. A formulation according to paragraph 10, wherein the formulation has a pH of about pH 6.0.

Paragraph 12. A formulation according to any one of the preceding paragraphs, wherein the ionic excipient is a salt.

Paragraph 13. A formulation according to paragraph 12, wherein the salt is arginine hydrochloride.

Paragraph 14. A formulation according to any one of the preceding paragraphs, wherein the ionic excipient is present at a concentration of about 75 mM to about 100 mM.

Paragraph 15. A formulation according to paragraph 14, wherein the ionic excipient is present at a concentration of about 80 mM.

Paragraph 16. A formulation according to any one of the preceding paragraphs, wherein the formulation further comprises a sugar.

Paragraph 17. A formulation according to paragraph 16, wherein the sugar is sucrose.

Paragraph 18. A formulation according to any one of paragraphs 16 to 17, wherein the sugar is present at a concentration of about 100 mM to about 140 mM.

Paragraph 19. A formulation according to paragraph 18, wherein the sugar is present at a concentration of about 120 mM.

Paragraph 20. A formulation according to any one of the preceding paragraphs, wherein the formulation further comprises one or more buffers.

Paragraph 21. A formulation according to paragraph 20, wherein the one or more buffers is selected from histidine, histidine hydrochloride, and histidine/histidine hydrochloride.

Paragraph 22. A formulation according to paragraph 21, wherein the one or more buffers is L-histidine/L-histidine hydrochloride monohydrate.

A formulation according to any one of paragraphs 20 to 23, wherein the one or more buffers is present at a concentration of about 10 mM to about 50 mM.

Paragraph 23. A formulation according to paragraph 23, wherein the one or more buffers is present at a concentration of about 30 mM.

Paragraph 24. A formulation according to any one of the preceding paragraphs, wherein the formulation further comprises a surfactant.
Paragraph 25. A formulation according to paragraph 25, wherein the surfactant is a polysorbate.
Paragraph 26. A formulation according to paragraph 26, wherein the surfactant is polysorbate-80.
Paragraph 27. A formulation according to any one of paragraphs 25 to 27, wherein the surfactant is present in the formulation at a concentration from about 0.001% (w/v) to about 0.07% (w/v).
Paragraph 28. A formulation according to paragraph 28, wherein the surfactant is present in the formulation at a concentration of about 0.02% (w/v).
Paragraph 29. A formulation according to any one of the preceding paragraphs, wherein the formulation further comprises one or more additional excipients, including for example, one or more sugars, salts, amino acids, polyols, chelating agents, emulsifiers and/or preservatives.
Paragraph 30. A formulation according to any one of paragraphs 1 to 29, which is a pharmaceutical formulation.
Paragraph 31. A pharmaceutical formulation according to paragraph 30 for use as a medicament.
Paragraph 32. A pharmaceutical formulation according to paragraph 31 for use in the treatment of a disease.
Paragraph 33. A method of treating or preventing a disease in a subject comprising administering a pharmaceutical formulation according to paragraph 31 to the subject.
Paragraph 34. An isolated monoclonal antibody having light chain CDR sequences:
CDR-L1 of SEQ ID NO: 3
CDR-L2 of SEQ ID NO: 4
CDR-L3 of SEQ ID NO: 5
and heavy chain CDR sequences:
CDR-H1 of SEQ ID NO: 6
CDR-H2 of SEQ ID NO: 7
CDR-H3 of SEQ ID NO: 8.
Paragraph 35. An isolated monoclonal antibody according to paragraph 35, wherein the monoclonal antibody has a light chain variable region sequence of SEQ ID NO: 9 and a heavy chain variable region sequence of SEQ ID NO: 10.
Paragraph 36. An isolated monoclonal antibody according to paragraph 35 or paragraph 36, wherein the monoclonal antibody has a light chain sequence of SEQ ID NO: 1 and a heavy chain sequence of SEQ ID NO: 2.
Paragraph 37. An isolated monoclonal antibody according to any one of paragraphs 35 to 37, wherein the antibody is an IgG1 antibody.
Paragraph 38. A pharmaceutical composition comprising an isolated antibody as defined in any one of paragraphs 35 to 38.
Paragraph 39. An isolated monoclonal antibody according to any one of paragraphs 35 to 38 or a pharmaceutical composition according to paragraph 39 for use as a medicament.
Paragraph 40. An isolated monoclonal antibody according to any one of paragraphs 35 to 38 or a pharmaceutical composition according to paragraph 39 for use in the treatment of a disease.
Paragraph 41. A method of treating or preventing a disease in a subject comprising administering an isolated monoclonal antibody according to any one of paragraphs 35 to 38 or a pharmaceutical composition according to paragraph 39 to the subject.
Paragraph 42. A lyophilized cake capable of being reconstituted using only sterile water into a formulation as defined in any one of paragraphs 1 to 31.
Paragraph 43. A composition capable of being lyophilized to form a lyophilized cake, wherein the lyophilized cake is capable of being reconstituted using only sterile water into a formulation as defined in any one of paragraphs 1 to 31.

What is claimed is:

1. A formulation comprising:
   an anti-Respiratory Syncytial Virus (RSV) monoclonal antibody;
   an ionic excipient; and
   one or more buffers;
   wherein the monoclonal antibody comprises light chain CDR sequences:
   CDR-L1 of SEQ ID NO: 3
   CDR-L2 of SEQ ID NO: 4
   CDR-L3 of SEQ ID NO: 5;
   and heavy chain CDR sequences:
   CDR-H1 of SEQ ID NO: 6
   CDR-H2 of SEQ ID NO: 7
   CDR-H3 of SEQ ID NO: 8;
   wherein the monoclonal antibody is present at a concentration of about 50 mg/ml or greater;
   wherein the ionic excipient is present at a concentration of about 50 mM to about 150 mM;
   wherein the one or more buffers is present at a concentration of about 10 mM to about 50 mM; and
   wherein the formulation has a pH of about 5.5 to about 7.5.

2. A formulation according to claim 1, wherein the monoclonal antibody comprises a light chain variable region sequence of SEQ ID NO: 9 and a heavy chain variable region sequence of SEQ ID NO: 10.

3. A formulation according to claim 1, wherein the monoclonal antibody comprises a light chain sequence of SEQ ID NO: 1 and a heavy chain sequence of SEQ ID NO: 2.

4. A formulation according to claim 1, wherein the ionic excipient is arginine hydrochloride.

5. A formulation according to claim 4, wherein the arginine hydrochloride is present at a concentration of about 80 mM.

6. A formulation according to claim 1, wherein the formulation further comprises a sugar.

7. A formulation according to claim 6, wherein the sugar is sucrose.

8. A formulation according to claim 7, wherein the sucrose is present at a concentration of about 100 mM to about 140 mM.

9. A formulation according to claim 7, wherein the sucrose is present at a concentration of about 120 mM.

10. A formulation according to claim 1, wherein the one or more buffers is selected from histidine, histidine hydrochloride, or a combination thereof.

11. A formulation according to claim 1, wherein the one or more buffers is present at a concentration of about 30 mM.

12. A formulation according to claim 11, wherein the one or more buffers is selected from L-histidine, L-histidine hydrochloride, or a combination thereof.

13. A formulation according to claim 1, wherein the formulation further comprises a surfactant.

14. A formulation according to claim 1, wherein the formulation further comprises polysorbate 80.

15. A formulation according to claim 14, wherein the polysorbate 80 is present at a concentration of from about 0.001% (w/v) to about 0.07% (w/v).

16. A formulation according to claim 14, wherein the polysorbate 80 is present at a concentration of about 0.02% (w/v) to about 0.04% (w/v).

17. A formulation according to claim 14, wherein the polysorbate 80 is present at a concentration of about 0.02% (w/v) or about 0.04% (w/v).

18. A formulation according to claim 1, wherein the monoclonal antibody is present at a concentration of about 100 mg/ml.

19. A formulation according to claim 1, wherein the formulation further comprises one or more additional excipients.

20. A formulation according to claim 19, wherein the one or more additional excipients is selected from one or more sugars, salts, amino acids, polyols, chelating agents, emulsifiers and/or preservatives.

21. A formulation according to claim 1, wherein the formulation has a pH in the range of about 5.7 to about 6.3.

22. A formulation according to claim 1, wherein the formulation has a pH of about 6.0.

23. A formulation according to claim 1, wherein the formulation is a pharmaceutical formulation.

24. A formulation according to claim 1, wherein the formulation is lyophilized.

25. A formulation according to claim 1, wherein the formulation is liquid.

26. A formulation comprising:
an anti-Respiratory Syncytial Virus (RSV) monoclonal antibody; and
an ionic excipient;
wherein the anti-RSV monoclonal antibody comprises a light chain comprising a CDR-L1 sequence of QASQDIVNYLN (SEQ ID NO: 3), a CDR-L2 sequence of VASNLET (SEQ ID NO: 4), and a CDR-L3 sequence of QQYDNLPLT of (SEQ ID NO: 5) and a heavy chain comprising a CDR-H1 sequence of DYIIN (SEQ ID NO: 6), a CDR-H2 sequence of GIIPVLGTVHYGPKFQG (SEQ ID NO: 7), and a CDR-H3 sequence of ETALVVSETYLPHYFDN (SEQ ID NO: 8);
wherein the monoclonal antibody is present at a concentration of about 75 mg/ml to about 200 mg/ml;
wherein the ionic excipient comprises arginine hydrochloride at a concentration of about 75 mM to about 100 mM;
wherein the formulation further comprises:
histidine, histidine hydrochloride, or a combination thereof at a concentration of about 10 mM to about 50 mM;
sucrose at a concentration of about 100 mM to about 140 mM; and
polysorbate 80 at a concentration of about 0.02% (w/v) to about 0.04% (w/v); and
wherein the formulation has a pH of about 5.5 to about 6.5.

27. A formulation according to claim 26, wherein the monoclonal antibody comprises a light chain variable region sequence of SEQ ID NO: 9 and a heavy chain variable region sequence of SEQ ID NO: 10.

28. A formulation comprising:
an anti-Respiratory Syncytial Virus (RSV) monoclonal antibody comprising a light chain sequence of SEQ ID NO: 1 and a heavy chain sequence of SEQ ID NO: 2;
wherein the monoclonal antibody is present at a concentration of about 75 mg/ml to about 200 mg/ml;
arginine hydrochloride at a concentration of about 80 mM;
histidine, histidine/histidine hydrochloride, or a combination thereof at a concentration of about 30 mM;
sucrose at a concentration of about 120 mM; and
polysorbate 80 at a concentration of about 0.02% (w/v) to about 0.04% (w/v); and
wherein the formulation has a pH of about 5.5 to about 6.5.

29. A formulation according to claim 1, wherein the monoclonal antibody comprises a light chain sequence of SEQ ID NO: 1 and a heavy chain sequence of SEQ ID NO: 2 and the formulation has a pH of about 5.7 to about 6.3.

30. A formulation according to claim 26, wherein the monoclonal antibody comprises a light chain sequence of SEQ ID NO: 1 and a heavy chain sequence of SEQ ID NO: 2.

* * * * *

UNITED STATES PATENT AND TRADEMARK OFFICE
CERTIFICATE OF CORRECTION

PATENT NO. : 11,286,294 B2
APPLICATION NO. : 17/351348
DATED : March 29, 2022
INVENTOR(S) : Brian Lobo and Deborah Goldberg It is certified that error appears in the above-identified patent and that said Letters Patent is hereby corrected as shown below:

In the Claims

In Claim 28, Column 38, Line 23, "histidine/histidine hydrochloride," should read --histidine hydrochloride,--.

Signed and Sealed this
Twenty-seventh Day of September, 2022

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 214
<212> TYPE: PRT
<213> ORGANISM: Artificial Sequence
<220> FEATURE:
<223> OTHER INFORMATION: Recombinant sequence

<400> SEQUENCE: 1

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 456
<212> TYPE: PRT
<213> ORGANISM: Artificial sequence
<220> FEATURE:
<223> OTHER INFORMATION: Recombinant sequence

<400> SEQUENCE: 2

Gln Val Gln Leu Val Gln Ser Gly Ala Glu Val Lys Lys Pro Gly Ser
1               5                   10                  15

Ser Val Met Val Ser Cys Gln Ala Ser Gly Gly Leu Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Glu Thr Tyr Leu Pro His Tyr
            100                 105                 110

Phe Asp Asn Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Tyr Ile Thr Arg Glu Pro Glu Val Thr Cys Val Val
```

```
                    260                 265                 270
Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 3
<211> LENGTH: 11
<212> TYPE: PRT
<213> ORGANISM: Artificial Sequence
<220> FEATURE:
<223> OTHER INFORMATION: Recombinant sequence

<400> SEQUENCE: 3

Gln Ala Ser Gln Asp Ile Val Asn Tyr Leu Asn
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Recombinant sequence

<400> SEQUENCE: 4

Val Ala Ser Asn Leu Glu Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Recombinant sequence

<400> SEQUENCE: 5

Gln Gln Tyr Asp Asn Leu Pro Leu Thr
1               5

<210> SEQ ID NO 6
```

```
<211> LENGTH: 5
<212> TYPE: PRT
<213> ORGANISM: Artificial Sequence
<220> FEATURE:
<223> OTHER INFORMATION: Recombinant sequence

<400> SEQUENCE: 6

Asp Tyr Ile Ile Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Recombinant sequence

<400> SEQUENCE: 7

Gly Ile Ile Pro Val Leu Gly Thr Val His Tyr Gly Pro Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Recombinant sequence

<400> SEQUENCE: 8

Glu Thr Ala Leu Val Val Ser Glu Thr Tyr Leu Pro His Tyr Phe Asp
1               5                   10                  15

Asn

<210> SEQ ID NO 9
<211> LENGTH: 107
<212> TYPE: PRT
<213> ORGANISM: Artificial Sequence
<220> FEATURE:
<223> OTHER INFORMATION: Recombinant sequence

<400> SEQUENCE: 9

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
                20                  25                  30

Leu Asn Trp Tyr Gln Gln Lys Pro Gly Lys Ala Pro Lys Leu Leu Ile
            35                  40                  45

Tyr Val Ala Ser Asn Leu Glu Thr Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 10
<211> LENGTH: 126
<212> TYPE: PRT
<213> ORGANISM: Artificial Sequence
<220> FEATURE:
<223> OTHER INFORMATION: Recombinant sequence
```

<400> SEQUENCE: 10

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

| Ser | Val | Met | Val | Ser | Cys | Gln | Ala | Ser | Gly | Gly | Leu | Leu | Glu | Asp | Tyr |
|---|---|---|---|---|---|---|---|---|---|---|---|---|---|---|---|
| | | | 20 | | | | | 25 | | | | | 30 | | |

| Ile | Ile | Asn | Trp | Val | Arg | Gln | Ala | Pro | Gly | Gln | Gly | Pro | Glu | Trp | Met |
|---|---|---|---|---|---|---|---|---|---|---|---|---|---|---|---|
| | | 35 | | | | | 40 | | | | | 45 | | | |

| Gly | Gly | Ile | Ile | Pro | Val | Leu | Gly | Thr | Val | His | Tyr | Gly | Pro | Lys | Phe |
|---|---|---|---|---|---|---|---|---|---|---|---|---|---|---|---|
| 50 | | | | | 55 | | | | | 60 | | | | | |

| Gln | Gly | Arg | Val | Thr | Ile | Thr | Ala | Asp | Glu | Ser | Thr | Asp | Thr | Ala | Tyr |
|---|---|---|---|---|---|---|---|---|---|---|---|---|---|---|---|
| 65 | | | | 70 | | | | | 75 | | | | | 80 | |

| Met | Glu | Leu | Ser | Ser | Leu | Arg | Ser | Glu | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Thr | Glu | Thr | Ala | Leu | Val | Val | Ser | Glu | Thr | Tyr | Leu | Pro | His | Tyr |
|---|---|---|---|---|---|---|---|---|---|---|---|---|---|---|---|
| | | | 100 | | | | | 105 | | | | | 110 | | |

| Phe | Asp | Asn | Trp | Gly | Gln | Gly | Thr | Leu | Val | Thr | Val | Ser | Ser |
|---|---|---|---|---|---|---|---|---|---|---|---|---|---|
| | | | 115 | | | | | 120 | | | | | 125 |

<210> SEQ ID NO 11
<211> LENGTH: 642
<212> TYPE: DNA
<213> ORGANISM: Artificial Sequence
<220> FEATURE:
<223> OTHER INFORMATION: Recombinant sequence

<400> SEQUENCE: 11

```
gacatccaga tgacccagtc cccctcctct ctgtctgctg ccgtgggcga cagagtgacc      60
atcacctgtc aggcctccca ggacatcgtg aactacctga actggtatca gcagaagccc     120
ggcaaggccc ccaagctgct gatctacgtg gcctccaacc tggaaaccgg cgtgccctcc     180
agattctccg gctctggctc tggcaccgac ttcagcctga ccatctccag cctgcagcct     240
gaggacgtgg ccacctacta ctgccagcag tacgacaacc tgcccctgac ctttggcgga     300
ggcaccaagg tggagatcaa acgaactgtg gctgcaccat ctgtcttcat cttcccccc      360
agcgacgagc agctgaagag cggcaccgcc tccgtggtgt gcctgctgaa caacttctac     420
ccccgcgagg ccaaggtgca gtggaaggtg gacaacgccc tgcagtccgg caacagccag     480
gagagcgtca ccgagcagga cagcaaggac tccacctaca gcctgagcag cacccctgacc    540
ctgagcaagg ccgactacga gaagcacaag gtgtacgcct gcgaggtgac ccaccagggc     600
ctgtccagcc ccgtgaccaa gagcttcaac aggggcgagt gc                        642
```

<210> SEQ ID NO 12
<211> LENGTH: 1368
<212> TYPE: DNA
<213> ORGANISM: Artificial Sequence
<220> FEATURE:
<223> OTHER INFORMATION: Recombinant sequence

<400> SEQUENCE: 12

```
caagtgcagc tggtgcagtc tggcgccgaa gtgaagaaac ccggctcctc cgtgatggtg      60
tcctgccagg cttctggcgg cctgctggaa gattacatca tcaactgggt gcgacaggcc     120
ccaggccagg gacctgaatg gatgggcgga atcatccccg tgctgggcac cgtgcactac     180
ggccctaagt tccagggcag agtgaccatc accgccgacg agtctaccga caccgcctac     240
atggaactgt cctccctgcg gagcgaggac accgccatgt actactgcgc caccgagaca     300
```

```
gccctggtgg tgtccgagac atacctgccc cactacttcg acaactgggg ccagggaacc    360
ctcgtgaccg tctcctcagc ctccaccaag ggcccatcgg tcttcccct ggcaccctcc     420 tccaagtcca cctccggcgg caccgccgct ctgggctgcc tggtgaagga ctacttccct    480
gagcctgtga ccgtgtcctg gaactctggc gccctgacct ctggcgtgca caccttccct    540
gccgtgctgc agtcctccgg cctgtactcc ctgtcctccg tggtgacagt gccttcctcc    600
tccctgggca cccagaccta catctgcaac gtgaaccaca agcccagcaa caccaaggtg    660
gacaagagag ttgagcccaa atcttgtgac aaaactcaca catgcccacc gtgcccagca    720
cctgaactcc tggggggacc gtcagtcttt ctgttccctc ctaagcctaa ggacaccctg    780
tacatcaccc gggagcctga agtgacctgc gtggtggtgg atgtgtccca cgaggaccct    840
gaggtgaagt tcaattggta cgtggacggc gtggaggtgc acaacgccaa gaccaagcct    900
cgggaggagc agtacaactc cacctaccgg gtggtgtctg tgctgaccgt gctgcaccag    960
gactggctga acggcaaaga atacaagtgc aaagtctcca acaaggccct gcctgccccc   1020
atcgagaaaa ccatctccaa agccaaaggg cagccccgag aaccacaggt gtacaccctg   1080
cctccctccc gcgaggagat gaccaagaac caggtgtccc tgacctgtct ggtgaagggc   1140
ttctaccctt ccgatatcgc cgtggagtgg gagtccaacg gccagcctga gaacaactac   1200
aagaccaccc ctcctgtgct ggactccgac ggctccttct tcctgtactc caagctgacc   1260
gtggacaagt cccggtggca gcagggcaac gtgttctcct gctccgtgat gcacgaggct   1320
ctgcacaacc actacaccca gaaaagcctc tccctgtctc cgggtaaa               1368
```